US008455516B2

(12) United States Patent (10) Patent No.: US 8,455,516 B2
Gochin et al. (45) Date of Patent: Jun. 4, 2013

(54) HIV-1 FUSION INHIBITORS AND METHODS

(75) Inventors: Miriam Gochin, San Francisco, CA (US); Guangyan Zhou, American Canyon, CA (US)

(73) Assignee: Touro University, Vallejo, CA (US)

( * ) Notice: Subject to any disclaimer, the term of this patent is extended or adjusted under 35 U.S.C. 154(b) by 0 days.

(21) Appl. No.: 13/006,716

(22) Filed: Jan. 14, 2011

(65) Prior Publication Data

US 2011/0190343 A1 Aug. 4, 2011

Related U.S. Application Data

(60) Provisional application No. 61/295,540, filed on Jan. 15, 2010.

(51) Int. Cl.
 *A61K 31/47* (2006.01)
 *A61K 31/404* (2006.01)
 *C07D 215/00* (2006.01)
 *C07D 209/04* (2006.01)

(52) U.S. Cl.
 USPC ........... 514/314; 514/414; 514/415; 546/173; 548/455; 548/469

(58) Field of Classification Search
 USPC ........... 514/314, 415, 414; 546/173; 548/455, 548/469
 See application file for complete search history.

(56) References Cited

U.S. PATENT DOCUMENTS

| 6,596,497 | B1 | 7/2003 | Jiang et al. |
| 6,858,600 | B2 | 2/2005 | Hamilton et al. |
| 7,241,803 | B2 | 7/2007 | Jiang et al. |
| 7,312,246 | B2 | 12/2007 | Hamilton et al. |
| 2004/0116427 | A1 | 6/2004 | Jiang et al. |
| 2005/0065066 | A1* | 3/2005 | Kaarsholm et al. ............... 514/3 |
| 2006/0287319 | A1 | 12/2006 | Jiang et al. |
| 2007/0232684 | A1 | 10/2007 | Jiang et al. |
| 2009/0069373 | A1* | 3/2009 | Wrobel et al. ............... 514/313 |

FOREIGN PATENT DOCUMENTS

| WO | WO2006/138118 | 12/2006 |
| WO | WO2008/030803 | 3/2008 |

OTHER PUBLICATIONS

CAS Registry No. 1161426-41-0, Accessed in STN Jun. 19, 2012.*
Cai, Lifeng, et al., "A Novel Fluorescence Intensity Screening Assay Identifies New Low-Molecular-Weight Inhibitors of the gp41 Coiled-Coil Domain of Human Immunodeficiency Virus Type 1," *Antimicrob. Agents Chemother.* 51(7), Jul. 2007, pp. 2388-2395.
Champagne, Kelly, et al., "Interactions of HIV-1 Inhibitory Peptide T20 with the gp41 N-HR Coiled Coil," *J. Biol. Chem.* 284(6), Feb. 6, 2009, pp. 3619-3627.
Debnath, Asim Kumar et al., "Structure-Based Identification of Small Molecule Antiviral Compounds Targeted to the gp41 Core Structure of the Human Immunodeficiency Virus Type 1," *J. Med. Chem._*42(17), Aug. 10, 1999, pp. 3203-3209.
Derdeyn, Cynthia A., et al., "Sensitivity of Human Immunodeficiency Virus Type 1 to the Fusion Inhibitor T-20 Is Modulated by Coreceptor Specificity Defined by the V3 Loop of gp120," *J. Virol.* 74(18), Sep. 2000, pp. 8358-8367.
Desmezieres, Emmanuel, et al., "Human Immunodeficiency Virus (HIV) gp41 Escape Mutants: Cross-Resistance to Peptide Inhibitors of HIV Fusion and Altered Receptor Activation of gp120," *J. Virol.* 79(8), Apr. 2005, pp. 4774-4781.
Ernst, Justin T. et al., "Design of a Protein Surface Antagonist Based on α-Helix Mimicry: Inhibition of gp41 Assembly and Viral Fusion." *Angew. Chem. Int. Ed.* 41(2), 2002, pp. 278-281.
Frey, Gary et al., "Small molecules that bind the inner core of gp41 and inhibit HIV envelope-mediated fusion," *PNAS* 103(38), Sep. 18, 2006, pp. 13938-13943.
Jiang, Shibo et al., "N-Substituted Pyrrole Derivatives as Novel Human Immunodeficiency Virus Type 1 Entry Inhibitors That Interfere with the gp41 Six-Helix Bundle Formation and Block Virus Fusion," *Antimicrob. Agents Chemother.* 48(11), Nov. 2004, pp. 4349-4359.
Jin, Bong-Suk et al., "High-Throughput Screening Method of Inhibitors that Block the Interaction between 2 Helical Regions of HIV-1 gp41," *J. Biomol. Screen.* 10(1), 2005, pp. 13-19.
Katrizky, Alan R. et al., "Design, Synthesis, and Structure-Activity Relationship of a Novel Series of 2-Aryl 5-(4-Oxo-3-phenethy1-2-thioxothiazolidinylidenemethyl)furans as HIV-1 Entry Inhibitors." *J. Med. Chem.* 52(23), Dec. 10, 2009, pp. 7631-7639.
Lackman-Smith, Carol, et al., "Development of a Comprehensive Human Immunodeficiency Virus Type 1 Screening Algorithm for Discovery and Preclinical Testing of Topical Microbicides," *Antimicrob. Agents Chemother.* 52(5), May 2008, pp. 1768-1781.
Lee-Huang, Sylvia et al., "Discovery of small-molecule HIV-1 fusion and integrase inhibitors oleuropein and hydroxytyrosol: Part I. Integrase inhibition," *Biochem. Biophys. Res. Comm.* 354, 2007, pp. 872-878.
Liu, Bin et al., "Structure-based design of substituted biphenyl ethylene ethers as ligands binding in the hydrophobic pocket of gp41 and blocking the helical bundle formation," *Bioorg. Med. Chem. Lett.*, Aug. 2009, 5 pp.
Liu, Kun et al., "Design, Synthesis, and Biological Evaluation of N-Carboxyphenylpyrrole Derivatives as Potent HIV Fusion Inhibitors Targeting gp41," *J. Med. Chem.* 51(24), Nov. 18, 2008, pp. 7843-7854.
Liu, Shuwen et al., "HIV Entry Inhibitors Targeting gp41: From Polypeptides to Small-Molecule Compounds," *Curr. Pharm. Des.* 13, 2007, pp. 143-162.
Liu, Shuwen et al., "Theaflavin derivatives in black tea and catechin derivatives in green tea inhibit HIV-1 entry by targeting gp41," *Biochim. Biophys. Acta* 1723, 2005, pp. 270-281.
Platt, Emily J., et al., "Kinetic Factors Control Efficiencies of Cell Entry, Efficacies of Entry Inhibitors, and Mechanisms of Adaptation of Human Immunodeficiency Virus," *J. Virol.* 79(7), Apr. 2005, pp. 4347-4356.

(Continued)

*Primary Examiner* — Samantha Shterengarts
(74) *Attorney, Agent, or Firm* — Weaver Austin Villeneuve & Sampson LLP

(57) ABSTRACT

A new series of HIV-1 fusion inhibitors and methods of use are disclosed. The compounds are based on a substituted indole, benzimidazole, indoline or isoindoline fragment. The compounds find use in inhibiting or preventing HIV fusion from occurring, thus inhibiting or preventing entry of viral RNA into host cells. The compounds may be useful towards other biological targets involving protein-protein interactions.

6 Claims, No Drawings

OTHER PUBLICATIONS

Stewart, Kent. D. et al., "Non-peptide Entry Inhibitors of HIV-1 that Target the gp41 Coiled-Coil Pocket," *Bioorg. Med. Chem. Lett.* 20(2), 2010, pp. 612-617.

Wang, Yong et al., "Structure-based design, synthesis and biological evaluation of new N-carboxyphenylpyrrole derivatives as HIV fusion inhibitors targeting gp41," *Bioorg. Med. Chem. Lett.*, Oct. 2009, 7 pp.

Wei, Xiping, et al., "Emergence of Resistant Human Immunodeficiency Virus Type 1 in Patients Receiving Fusion Inhibitor (T-20) Monotherapy,"*Antimicrob. Agents Chemother.* 46(6), Jun. 2002, pp. 1896-1905.

Welch, Brett D. et al., "Potent D-peptide inhibitors of HIV-1 entry," *PNAS* 104(43), Oct. 23, 2007, pp. 16828-16833.

Xu, Yang et al., "Evaluation of 'Credit Card' Libraries for Inhibition of HIV-1 gp41 Fusogenic Core Formation," *J. Comb. Chem.* 8, Apr. 22, 2006, pp. 531-539.

Zhou, Genfa, et al., "The Structure of an HIV-1 Specific Cell Entry Inhibitor in Complex with the HIV-1 gp41 Trimeric Core," *Bioorg. Med. Chem.* 8, 2000, pp. 2219-2228.

\* cited by examiner

HIV-1 FUSION INHIBITORS AND METHODS

CROSS-REFERENCE TO RELATED APPLICATIONS

This application claims the benefit of and priority to U.S. Provisional Application Ser. No. 61/295,540 filed Jan. 15, 2010, the contents of which are incorporated herein by reference in their entirety and for all purposes.

STATEMENT AS TO RIGHTS TO INVENTIONS MADE UNDER FEDERALLY SPONSORED RESEARCH AND DEVELOPMENT

This invention was made with government support under NIH grant nos. NS059403 and NS066469. The Government has certain rights in the invention.

FIELD OF INVENTION

The invention generally relates to Human Immunodeficiency Virus-1 (HIV-1) fusion inhibitors and methods of use.

BACKGROUND

Human Immunodeficiency Virus (HIV) is a retrovirus that infects the immune system of humans. The viral genome becomes integrated within the cellular DNA, resulting in chronic permanent infection. Although virus may remain latent for a period of time, eventually the immune system becomes overwhelmed, causing severe opportunistic infections and neoplasms, in the absence of antiretroviral therapy. Current antiretroviral therapy consists of drugs targeted to steps in the viral life cycle that occur subsequent to infection of the cell, such as HIV integrase, HIV reverse transcriptase, HIV protease inhibitors. One of the main problems is the high mutability of HIV, so that drug-resistant strains rapidly develop, increasing the risk of treatment failure. This is mitigated by using a cocktail of drugs targeting different viral proteins.

Currently there is one FDA-approved entry inhibitor targeting the human CCR5 receptor, which HIV uses as a coreceptor for entry. The HIV envelope glycoprotein transmembrane subunit gp41 also plays an indispensable role in entry, by being responsible for viral fusion. The core of the gp41 hairpin consists of a parallel trimeric coiled-coil of N-terminal heptad repeats (NHR) with the C-terminal heptads repeat (CHR) wrapped down the outside in an anti-parallel fashion.

Fuzeon® (a registered trademark of Hoffmann-La Hoffman LaRoche Inc., of Nutley, N.J.), also called T20, was approved by the FDA as the first in a new class of anti-HIV drugs—HIV fusion inhibitors. It is believed to interact with the gp41 NHR and block the fusion between the viral and the target cell membranes (see Champagne, K.; Shishido, A.; Root, M. J. Interactions of HIV-1 inhibitory peptide T20 with the GP41 N-HR coiled coil. *J Biol Chem* 2008). However peptidic therapeutics suffer from low or non-existent oral bioavailability and high cost, which limit their clinical application. Given the severity and prevalence of HIV infection in humans, new therapies are needed.

SUMMARY

The present invention provides compounds, methods of making the compounds, and methods of using the compounds in the treatment of conditions in which inhibiting HIV-1 fusion is therapeutically useful. The compounds find particular use in treating humans infected with HIV, exposed to HIV, or at risk for HIV infection, alone or in combination with other agents.

One aspect is a compound of Formula I,

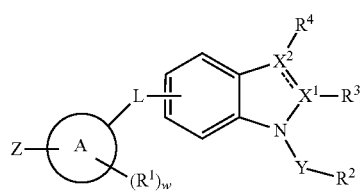

or a pharmaceutically acceptable salt thereof, wherein:

A is a $C_{6-10}$aryl or a 5-15 membered heteroaryl;

L is a bond, —N($R^a$)—, —O—, —S—, —S(O)—, —$SO_2$—, $C_{1-3}$alkylene or —O$C_{1-3}$alkylene;

Y is a bond or $C_{1-3}$alkylene;

Z is —$CO_2R^a$, —$SO_3R^a$, —$OSO_3R^a$, —$PO_3R^a$, —$OPO_3R^a$, —B(O$R^a$)$_2$, —OH, —S(O)$_2$N(H)—C(O)$R^a$, tetrazolyl, —C(O)N($R^a$)—OH, —C(N=OH)—$R^a$ or H;

when Z is H, then at least one of $R^2$, $R^3$ or $R^4$ bears a group selected from —$CO_2R^a$, —$SO_3R^a$, —$OSO_3R^a$, —$PO_3R^a$, —$OPO_3R^a$, —B(O$R^a$)$_2$, —OH, —S(O)$_2$N(H)—C(O)$R^a$, tetrazolyl, —C(O)N($R^a$)OH and —C(N=OH)—$R^a$;

when the bond between $X^1$ and $X^2$ is a single bond, $X^1$ and $X^2$ are independently CH or N, provided $X^1$ and $X^2$ are not simultaneously N;

when the bond between $X^1$ and $X^2$ is a double bond, $X^1$ and $X^2$ are independently C or N, provided $X^1$ and $X^2$ are not simultaneously N and provided, when $X^1$ or $X^2$ is N, then $R^3$ or $R^4$ is absent, respectively;

each $R^1$ is independently optionally substituted —$R^a$, halo, optionally substituted —O$R^a$, —O—(C($R^a$)$_2$)$_m$—O$R^a$, $C_{1-3}$haloalkyloxy, —S$R^a$, —N($R^c$)$_2$, —CF$_3$, —CN, —OCN, —SCN, —NO, —NO$_2$, —N$_3$, —S(O)$R^a$, —S(O)$_2R^a$, —S(O)$_2$N($R^c$)$_2$, —C(O)$R^a$, —C(O)N($R^c$)$_2$ or —OC(O)$R^a$;

each of $R^2$, $R^3$ and $R^4$ are, independently, —H, —C(O)CO$_2R^a$, —C(O)H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl;

each $R^a$ is independently H, $C_{1-6}$alkyl, $C_{3-8}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl;

each $R^c$ is independently $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;

each $R^d$ is =O, —$C_{1-6}$alkyl, —O$R^a$, —OCF$_3$, =S, —S$R^a$, =N$R^a$, =NO$R^a$, —N($R^a$)$_2$, halo, —CF$_3$, —CN, —NC, —OCN, —SCN, —NO, —NO$_2$, =N$_2$, —N$_3$, —S(O)

$R^a$, —$S(O_2)R^a$, —$SO_3R^a$, —$S(O)N(R^a)_2$, —$S(O)_2N(R^a)_2$, —$OS(O)R^a$, —$OS(O)_2R^a$, —$OSO_3R^a$, —$OS(O)_2N(R^a)_2$, —$C(O)R^a$, —$CO_2R^a$, —$C(O)N(R^a)_2$, —$C(NR^a)N(R^a)_2$, —$C(NOH)R^a$, —$C(NOH)N(R^a)_2$, —$OCO_2R^a$, —$OC(O)N(R^a)_2$, —$OC(NR^a)N(R^a)_2$, —$[N(R^a)C(O)]_nR^a$, —$(C(R^a)_2)_n$—$OR^a$, —$N(R^a)$—$S(O)_2R^a$, —$C(O)$—$C_{1-6}$haloalkyl, —$S(O)_2C_{1-6}$haloalkyl, —$OC(O)R^a$, —$O(C(R^a)_2)_m$—$OR^a$, —$S(C(R^a)_2)_m$—$OR^a$, —$N(R^a)C_{1-6}$haloalkyl, —$P(O)(OR^a)_2$, —$N(R^a)$—$(C(R^a)_2)_m$—$OR^a$, —$[N(R^a)C(O)]_nOR^a$, —$[N(R^a)C(O)]_nN(R^a)_2$, —$[N(R^a)C(NR^a)]_nN(R^a)_2$ or —$N(R^a)C(O)C_{1-6}$haloalkyl;

optionally two $R^d$, taken together with the atom or atoms to which they are attached, combine to form a 3-10 membered partially or fully saturated mono or bicyclic ring, optionally containing one or more heteroatoms and optionally substituted with one or more $R^a$;

w is 0, 1, 2, 3 or 4;

each m is 1, 2 or 3; and each n is 0, 1, 2 or 3.

In one embodiment, A is selected from the group consisting of phenyl, pyridyl, pyrimidinyl, pyrazinyl, indolyl, benzimidazolyl, indazolyl, quinolyl, napthalenyl, isoquinolyl and quinazolinyl. In this embodiment, the bicyclic ring system including $X^1$ and $X^2$ is an indole, a benzimidazole, an indazole or an indoline. Various substitutions on ring A or the ring incorporating $X^1$ and $X^2$ are discussed in more detail below. One embodiment is a compound according to formula I where L is —$OC_{1-3}$alkylene and the remaining variables are as described. One embodiment is a compound according to formula I where L is —O— and the remaining variables are as described. In one embodiment, at least one of $R^1$ is optionally substituted —$OR^a$, where Z is H or non-H. Pharmaceutical compositions are also disclosed.

Another embodiment is a compound or pharmaceutical composition disclosed herein for use in inhibiting HIV-1 cell fusion. Pharmaceutical compositions are described in more detail below.

Another embodiment is a compound or pharmaceutical composition disclosed herein for use in inhibiting HIV-1 infectivity.

Another embodiment is a compound or pharmaceutical composition disclosed herein for use in treating a symptom or effect of HIV-1 infection in a subject.

Compounds described herein are inhibitors of HIV-1 fusion and as a consequence of this activity, the compounds can be used in a variety of in vitro, in vivo, and ex vivo contexts to regulate or inhibit HIV-1 fusion.

One embodiment is a method of inhibiting HIV-1 cell fusion, the method including contacting cells with an effective amount of a compound or pharmaceutical composition disclosed herein.

Another embodiment is a method of inhibiting HIV-1 infectivity, the method including contacting cells with an effective amount of a compound or pharmaceutical composition disclosed herein.

Another embodiment is a method of treating a symptom or effect of HIV-1 infection in a subject, the method including administering to the subject an effective amount of a compound or pharmaceutical composition disclosed herein. A more specific embodiment includes co-administration of an agent that mitigates a symptom or effect of HIV-1 infection.

Another embodiment is use of a compound or pharmaceutical composition disclosed herein in the manufacture of a medicament for inhibiting HIV-1 cell fusion.

Another embodiment is use of a compound or pharmaceutical composition disclosed herein to inhibit HIV-1 infectivity.

Another embodiment is use of a compound or pharmaceutical composition disclosed herein to treat a symptom or effect of HIV-1 infection in a subject.

These and other features and advantages of the present invention will be described in more detail below.

DETAILED DESCRIPTION

In the following detailed description of the present invention, numerous specific embodiments are set forth in order to provide a thorough understanding of the invention. However, as will be apparent to those skilled in the art, the present invention may be practiced without these specific details or by using alternate elements or processes. In other instances well-known processes, procedures and components have not been described in detail so as not to unnecessarily obscure aspects of the present invention.

Overview

The invention encompasses compounds described herein, for example of Formula I, and the compositions and methods using these compounds in the treatment of conditions in which inhibiting HIV-1 fusion is therapeutically useful.

Terms

As used herein, the following words and phrases are intended to have the meanings as set forth below, except to the extent that the context in which they are used indicates otherwise or they are expressly defined to mean something different.

The symbol "—" means a single bond, "═" means a double bond, "≡" means a triple bond. The symbol "⌇" refers to a group on a double-bond as occupying either position on the terminus of the double bond to which the symbol is attached; that is, the geometry, E- or Z-, of the double bond is ambiguous and both isomers are meant to be included. When a group is depicted removed from its parent formula, the "⌇" symbol will be used at the end of the bond which was theoretically cleaved in order to separate the group from its parent structural formula.

When chemical structures are depicted or described, unless explicitly stated otherwise, all carbons are assumed to have hydrogen substitution to conform to a valence of four. For example, in the structure on the left-hand side of the schematic below there are nine hydrogens implied. The nine hydrogens are depicted in the right-hand structure. Sometimes a particular atom in a structure is described in textual formula as having a hydrogen or hydrogens as substitution (expressly defined hydrogen), for example, —$CH_2CH_2$—. It would be understood by one of ordinary skill in the art that the aforementioned descriptive techniques are common in the chemical arts to provide brevity and simplicity to description of otherwise complex structures.

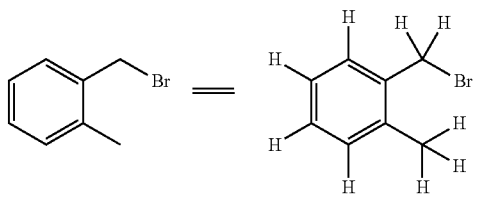

In this application, some ring structures are depicted generically and will be described textually. For example, in the schematic below if ring A is used to describe a phenyl, there are at most four hydrogens on ring A (when R is not H).

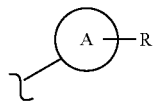

In compounds of Formula I, substituents $R^3$ and $R^4$ are depicted bonded to $X^1$ and $X^2$, respectively. This means that when $X^1$ and/or $X^2$ are sp$^2$ carbons (the dotted double line indicating the possibility that there is a single or a double bond between $X^1$ and $X^2$) that $R^3$ and $R^4$ exist and are defined as disclosed herein. When a double bond between $X^1$ and $X^2$ exists, and $X^1$ is N, then $R^3$ does not exist. When a double bond between $X^1$ and $X^2$ exists, and $X^2$ is N, then $R^4$ does not exist. When a single bond between $X^1$ and $X^2$ exists, and $X^1$ is N, then $R^3$ is as defined herein so long as a stable structure is formed. When a single bond between $X^1$ and $X^2$ exists, and $X^2$ is N, then $R^4$ is as defined herein so long as a stable structure is formed. When a single bond between $X^1$ and $X^2$ exists, and $X^1$ is CH, then $R^3$ is as defined herein. When a single bond between $X^1$ and $X^2$ exists, and $X^2$ is CH, then $R^4$ is as defined herein.

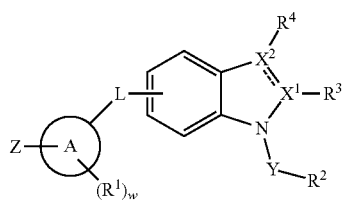

If a group R is depicted as "floating" on a ring system, as for example in formula I where Z and $R^1$ are floating on ring A, then the respective groups Z and $R^1$ can be substituted on any part of ring A. For example, if ring A is a fused ring system, for example an indolyl, then Z and $R^1$ (how many defined by w) can reside on different ring fusion partners that comprise ring A. Some examples are illustrated below. In the example depicted, the groups can reside on an atom in either the 5-membered or the 6-membered ring of the indolyl ring system so long it results in a stable structure.

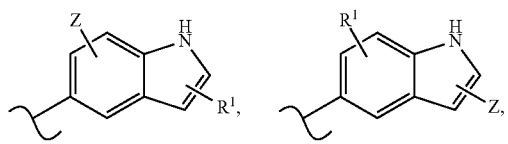

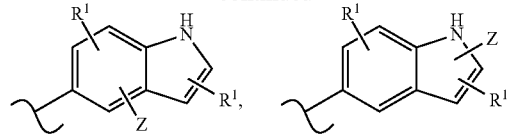

When there are more than one such depicted "floating" groups, as for example in the formulae:

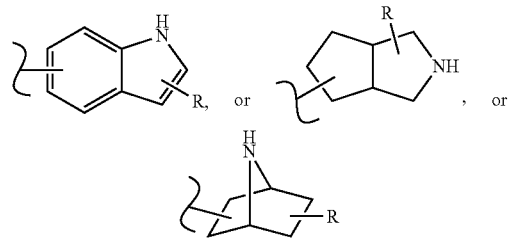

where there are two groups, namely, the R and the bond indicating attachment to a parent structure; then, unless otherwise defined, the "floating" groups can reside on any atoms of the ring system, again assuming each replaces a depicted, implied, or expressly defined hydrogen on the ring system and a chemically stable compound would be formed by such an arrangement.

When a group R is depicted as existing on a ring system containing saturated carbons, as for example in the formula:

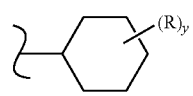

where, in this example, y can be more than one, assuming each replaces a currently depicted, implied, or expressly defined hydrogen on the ring; then, unless otherwise defined, two R's can reside on the same carbon. A simple example is when R is a methyl group; there can exist a geminal dimethyl on a carbon of the depicted ring (an "annular" carbon). In another example, two R's on the same carbon, including that same carbon, can form a ring, thus creating a spirocyclic ring (a "spirocyclyl" group) structure. Using the previous example, where two R's form, e.g. a piperidine ring in a spirocyclic arrangement with the cyclohexane, as for example in the formula:

"Alkyl" in its broadest sense is intended to include linear, branched, or cyclic hydrocarbon structures, and combinations thereof. Alkyl groups can be fully saturated or with one or more units of unsaturation, but not aromatic. Generally alkyl groups are defined by a subscript, either a fixed integer or a range of integers. For example, "C$_8$alkyl" includes n-octyl, iso-octyl, 3-octynyl, cyclohexenylethyl, cyclohexylethyl, and the like; where the subscript "8" designates that all groups defined by this term have a fixed carbon number of eight. In another example, the term "C$_{1-6}$alkyl" refers to alkyl groups having from one to six carbon atoms and, depending on any unsaturation, branches and/or rings, the requisite number of hydrogens. Examples of $C_{1-6}$alkyl groups include methyl, ethyl, vinyl, propyl, isopropyl, butyl, s-butyl, t-butyl, isobutyl, isobutenyl, pentyl, pentynyl, hexyl, cyclohexyl, hexenyl, and the like. When an alkyl residue having a specific number of carbons is named generically, all geometric isomers having that number of carbons are intended to be encompassed. For example, either "propyl" or "$C_3$alkyl" each include n-propyl, c-propyl, propenyl, propynyl, and isopropyl. Cycloalkyl is a subset of alkyl and includes cyclic hydrocarbon groups of from three to thirteen carbon atoms. Examples of cycloalkyl groups include c-propyl, c-butyl, c-pentyl, norbornyl, norbornenyl, c-hexenyl, adamantyl and the like. As mentioned, alkyl refers to alkanyl, alkenyl, and alkynyl residues (and combinations thereof)—it is intended to include, e.g., cyclohexylmethyl, vinyl, allyl, isoprenyl, and the like. An alkyl with a particular number of carbons can be named using a more specific but still generic geometrical constraint, e.g. "$C_{3-6}$cycloalkyl" which means only cycloalkyls having between 3 and 6 carbons are meant to be included in that particular definition. Unless specified otherwise, alkyl groups, whether alone or part of another group, e.g. —C(O)alkyl, have from one to twenty carbons, that is $C_{1-20}$alkyl. In the example "—C(O)alkyl," where there were no carbon count limitations defined, the carbonyl of the —C(O)alkyl group is not included in the carbon count, since "alkyl" is designated generically. But where a specific carbon limitation is given, e.g. in the term "optionally substituted $C_{1-20}$alkyl," where the optional substitution includes "oxo" the carbon of any carbonyls formed by such "oxo" substitution are included in the carbon count since they were part of the original carbon count limitation. However, again referring to "optionally substituted $C_{1-20}$alkyl," if optional substitution includes carbon-containing groups, e.g. —$CH_2CO_2H$, the two carbons in this group are not included in the $C_{1-20}$alkyl carbon limitation.

When a carbon number limit is given at the beginning of a term which itself comprises two terms, the carbon number limitation is understood as inclusive for both terms. For example, for the term "$C_{7-14}$arylalkyl," both the "aryl" and the "alkyl" portions of the term are included the carbon count, a maximum of 14 in this example, but additional substituent groups thereon are not included in the atom count unless they incorporate a carbon from the group's designated carbon count, as in the "oxo" example above. Likewise when an atom number limit is given, for example "6-14 membered heteroarylalkyl," both the "heteroaryl" and the "alkyl" portion are included the atom count limitation, but additional substituent groups thereon are not included in the atom count unless they incorporate a carbon from the group's designated carbon count. In another example, "$C_{4-10}$cycloalkylalkyl" means a cycloalkyl bonded to the parent structure via an alkylene, alkylidene or alkylidyne; in this example the group is limited to 10 carbons inclusive of the alkylene, alkylidene or alkylidyne subunit. As another example, the "alkyl" portion of, e.g. "$C_{7-14}$arylalkyl" is meant to include alkylene, alkylidene or alkylidyne, unless stated otherwise, e.g. as in the terms "$C_{7-14}$arylalkylene" or "$C_{6-10}$aryl-$CH_2CH_2$—."

"Alkylene" refers to straight, branched and cyclic (and combinations thereof) divalent radical consisting solely of carbon and hydrogen atoms, containing no unsaturation and having from one to ten carbon atoms, for example, methylene, ethylene, propylene, n-butylene and the like. Alkylene is like alkyl, referring to the same residues as alkyl, but having two points of attachment and, specifically, fully saturated. Examples of alkylene include ethylene (—$CH_2CH_2$—), propylene (—$CH_2CH_2CH_2$—), dimethylpropylene (—$CH_2C(CH_3)_2CH_2$—), cyclohexan-1,4-diyl and the like. A group such as "—O—O$C_{1-3}$alkylene" is a bivalent group where the oxygen end and the carbon end of the group can link either of the two parts of a molecule described as including the bivalent linking group. For example, if R and a phenyl group are linked by "—O$C_{1-3}$alkylene," then both R—O$C_{1-3}$alkylene-phenyl and phenyl-O$C_{1-3}$alkylene-R are meant to be included.

"Alkylidene" refers to straight, branched and cyclic (and combinations thereof) unsaturated divalent radical consisting solely of carbon and hydrogen atoms, having from two to ten carbon atoms, for example, ethylidene, propylidene, n-butylidene, and the like. Alkylidene is like alkyl, referring to the same residues as alkyl, but having two points of attachment and, specifically, at least one unit of double bond unsaturation. Examples of alkylidene include vinylidene (—CH═CH—), cyclohexylvinylidene (—CH═C($C_6H_{13}$)—), cyclohexen-1,4-diyl and the like.

"Alkylidyne" refers to straight, branched and cyclic (and combinations thereof) unsaturated divalent radical consisting solely of carbon and hydrogen atoms having from two to ten carbon atoms, for example, propylid-2-ynyl, n-butylid-1-ynyl, and the like. Alkylidyne is like alkyl, referring to the same residues as alkyl, but having two points of attachment and, specifically, at least one unit of triple bond unsaturation.

Any of the above radicals "alkylene," "alkylidene" and "alkylidyne," when optionally substituted, can contain alkyl substitution which itself can contain unsaturation. For example, 2-(2-phenylethynyl-but-3-enyl)-naphthalene (IUPAC name) contains an n-butylid-3-ynyl radical with a vinyl substituent at the 2-position of the radical. Combinations of alkyls and carbon-containing substitutions thereon are limited to thirty carbon atoms.

"Alkoxy" refers to the group —O-alkyl, where alkyl is as defined herein. Alkoxy includes, by way of example, methoxy, ethoxy, n-propoxy, isopropoxy, n-butoxy, t-butoxy, sec-butoxy, n-pentoxy, cyclohexyloxy, cyclohexenyloxy, cyclopropylmethyloxy, and the like.

"Acyl" refers to the groups —C(O)H, —C(O)alkyl, —C(O)aryl and —C(O)heterocyclyl.

"Amino" refers to the group —$NH_2$.

"Amide" refers to the group —C(O)$NH_2$ or —N(H)acyl.

"Aryl" (sometimes referred to as "Ar") refers to a monovalent aromatic carbocyclic group of, unless specified otherwise, from 6 to 15 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, 9,10-dihydrophenanthrenyl, indanyl, tetralinyl, and fluorenyl and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic.

"Arylene" refers to an aryl that has at least two groups attached thereto. For a more specific example, "phenylene" refers to a divalent phenyl ring radical. A phenylene, thus can have more than two groups attached, but is defined by a minimum of two non-hydrogen groups attached thereto.

"Arylalkyl" refers to a residue in which an aryl moiety is attached to a parent structure via one of an alkylene, alkylidene, or alkylidyne radical. Examples include benzyl, phenethyl, phenylvinyl, phenylallyl and the like. When specified as "optionally substituted," both the aryl, and the corresponding alkylene, alkylidene, or alkylidyne portion of an arylalkyl group can be optionally substituted. By way of example, "C$_{7-11}$arylalkyl" refers to an arylalkyl limited to a total of eleven carbons, e.g., a phenylethyl, a phenylvinyl, a phenylpentyl and a naphthylmethyl are all examples of a "C$_{7-11}$arylalkyl" group.

"Aryloxy" refers to the group —O-aryl, where aryl is as defined herein, including, by way of example, phenoxy, naphthoxy, and the like.

"Carboxyl," "carboxy" or "carboxylate" refers to —CO$_2$H or salts thereof.

"Carboxyl ester" or "carboxy ester" or "ester" refers to the group —CO$_2$alkyl, —CO$_2$aryl or —CO$_2$heterocyclyl.

"Carbonate" refers to the group —OCO$_2$alkyl, —OCO$_2$aryl or —OCO$_2$heterocyclyl.

"Carbamate" refers to the group —OC(O)NH$_2$, —N(H)carboxyl or —N(H)carboxyl ester.

"Cyano" or "nitrile" refers to the group —CN.

"Formyl" refers to the specific acyl group —C(O)H.

"Halo" or "halogen" refers to fluoro, chloro, bromo and iodo.

"Haloalkyl" and "haloaryl" refer generically to alkyl and aryl radicals that are substituted with one or more halogens, respectively. By way of example "dihaloaryl," "dihaloalkyl," "trihaloaryl" etc. refer to aryl and alkyl substituted with a plurality of halogens, but not necessarily a plurality of the same halogen; thus 4-chloro-3-fluorophenyl is a dihaloaryl group.

"Perhalo" as a modifier means that the group so modified has all its available hydrogens replaced with halogens. An example would be "perhaloalkyl." Perhaloalkyls include —CF$_3$, —CF$_2$CF$_3$, perchloroethyl and the like.

"Hydroxy" or "hydroxyl" refers to the group —OH.

"Heteroatom" refers to O, S, N, or P.

"Heterocyclyl" in the broadest sense includes aromatic and non-aromatic ring systems and more specifically refers to a stable three- to fifteen-membered ring radical that consists of carbon atoms and from one to five heteroatoms. For purposes of this invention, the heterocyclyl radical can be a monocyclic, bicyclic or tricyclic ring system, which can include fused or bridged ring systems as well as spirocyclic systems; and the nitrogen, phosphorus, carbon or sulfur atoms in the heterocyclyl radical can be optionally oxidized to various oxidation states. In a specific example, the group —S(O)$_{0-2}$—, refers to —S— (sulfide), —S(O)— (sulfoxide), and —SO$_2$— (sulfone) linkages. For convenience, nitrogens, particularly but not exclusively, those defined as annular aromatic nitrogens, are meant to include their corresponding N-oxide form, although not explicitly defined as such in a particular example. Thus, for a compound having, for example, a pyridyl ring; the corresponding pyridyl-N-oxide is meant to be included as another compound of the invention. In addition, annular nitrogen atoms can be optionally quaternized. "Heterocycle" includes heteroaryl and heteroalicyclyl, that is a heterocyclic ring can be partially or fully saturated or aromatic. Thus a term such as "heterocyclylalkyl" includes heteroalicyclylalkyls and heteroarylalkyls. Examples of heterocyclyl radicals include, but are not limited to, azetidinyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothieliyl, thiamorpholinyl, thiamorpholinyl sulfoxide, thiamorpholinyl sulfone, dioxaphospholanyl, and oxadiazolyl.

"Heteroaryl" refers to an aromatic group having from 1 to 10 annular carbon atoms and 1 to 4 annular heteroatoms. Heteroaryl groups have at least one aromatic ring component, but heteroaryls can be fully unsaturated or partially unsaturated. If any aromatic ring in the group has a heteroatom, then the group is a heteroaryl, even, for example, if other aromatic rings in the group have no heteroatoms. For example, 2H-pyrido[3,2-b][1,4]oxazin-3(4H)-one-7-yl, indolyl and benzimidazolyl are "heteroaryls." Heteroaryl groups can have a single ring (e.g., pyridinyl, imidazolyl or furyl) or multiple condensed rings (e.g., indolizinyl, quinolinyl, benzimidazolyl or benzothienyl), where the condensed rings may or may not be aromatic and/or contain a heteroatom, provided that the point of attachment to the parent molecule is through an atom of the aromatic portion of the heteroaryl group. In one embodiment, the nitrogen and/or sulfur ring atom(s) of the heteroaryl group are optionally oxidized to provide for the N-oxide (N→O), sulfinyl, or sulfonyl moieties. Compounds described herein containing phosphorous, in a heterocyclic ring or not, include the oxidized forms of phosphorous. Heteroaryl groups are monocyclic, bicyclic, tricyclic or tetracyclic.

"Heteroaryloxy" refers to —O-heteroaryl.

"Heteroarylene" generically refers to any heteroaryl that has at least two groups attached thereto. For a more specific example, "pyridylene" refers to a divalent pyridyl ring radical. A pyridylene, thus can have more than two groups attached, but is defined by a minimum of two non-hydrogen groups attached thereto.

"Heteroalicyclic" refers specifically to a non-aromatic heterocyclyl radical. A heteroalicyclic may contain unsaturation, but is not aromatic. As mentioned, aryls and heteroaryls are attached to the parent structure via an aromatic ring. So, e.g., 2H-1,4-benzoxazin-3(4H)-one-4-yl is a heteroalicyclic, while 2H-1,4-benzoxazin-3(4H)-one-7-yl is an aryl. In another example, 2H-pyrido[3,2-b][1,4]oxazin-3(4H)-one-4-yl is a heteroalicyclic, while 2H-pyrido[3,2-b][1,4]oxazin-3(4H)-one-7-yl is a heteroaryl.

"Heterocyclylalkyl" refers to a heterocyclyl group linked to the parent structure via e.g. an alkylene linker, for example (tetrahydrofuran-3-yl)methyl- or (pyridin-4-yl)methyl

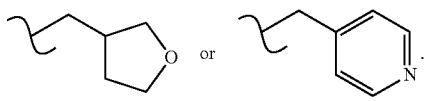

"Heterocyclyloxy" refers to the group —O-heterocycyl.

"Nitro" refers to the group —NO$_2$.

"Oxo" refers to a double bond oxygen radical, =O.

"Oxy" refers to —O. radical (also designated as →O), that is, a single bond oxygen radical. By way of example, N-oxides are nitrogens bearing an oxy radical.

When a group with its bonding structure is denoted as being bonded to two partners; that is, a divalent radical, for example, —OCH$_2$—, then it is understood that either of the two partners can be bound to the particular group at one end, and the other partner is necessarily bound to the other end of the divalent group, unless stated explicitly otherwise. Stated another way, divalent radicals are not to be construed as limited to the depicted orientation, for example "—OCH$_2$—" is meant to mean not only "—OCH$_2$—" as drawn, but also "—CH$_2$O—."

"Optional" or "optionally" means that the subsequently described event or circumstance may or may not occur, and that the description includes instances where said event or circumstance occurs and instances in which it does not. One of ordinary skill in the art would understand that, with respect to any molecule described as containing one or more optional substituents, that only synthetically feasible compounds are meant to be included. "Optionally substituted" refers to all subsequent modifiers in a term, for example in the term "optionally substituted arylC$_{1-8}$alkyl," optional substitution may occur on both the "C$_{1-8}$alkyl" portion and the "aryl" portion of the arylC$_{1-8}$alkyl group. Also by way of example, optionally substituted alkyl includes optionally substituted cycloalkyl groups. The term "substituted," when used to modify a specified group or radical, means that one or more hydrogen atoms of the specified group or radical are each, independently of one another, replaced with the same or different substituent groups as defined below. Thus, when a group is defined as "optionally substituted" the definition is meant to encompass when the groups is substituted with one or more of the radicals defined below, and when it is not so substituted.

Substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —N(R$^{80}$)$_2$, perhaloalkyl, —CN, —OCN, —SCN, —NO, —NO$_2$, =N$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —P(O)(O$^-$)$_2$(M)$_2$, —P(O)(O$^-$)$_2$M$^{2+}$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2$$^-$M$^+$, —CO$_2$R$^{70}$, —C(S)OR$^{70}$, —C(O)N(R$^{80}$)$_2$, —C(NR$^{70}$)(R$^{80}$)$_2$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$ is alkyl, heterocyclyl, heterocyclylalkyl, aryl or arylalkyl; each R$^{70}$ is independently hydrogen or R$^{60}$; each R$^{80}$ is independently R$^{70}$ or alternatively, two R$^{80}$'s, taken together with the nitrogen atom to which they are bonded, form a 3 to 7-membered heteroalicyclyl which optionally includes from 1 to 4 of the same or different additional heteroatoms selected from O, N and S, of which N optionally has H or C$_1$-C$_3$alkyl substitution; and each M is a counter ion with a net single positive charge. Each M is independently, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ (a subscript 0.5 means e.g. that one of the counter ions for such divalent alkali earth ions can be an ionized form of a compound described herein and the other a typical counter ion such as chloride, or two ionized compounds can serve as counter ions for such divalent alkali earth ions, or a doubly ionized compound can serve as the counter ion for such divalent alkali earth ions). As specific examples, —N(R$^{80}$)$_2$ is meant to include —NH$_2$, —NH-alkyl, N-pyrrolidinyl, N-piperazinyl, 4N-methyl-piperazin-1-yl and N-morpholinyl.

Substituent groups for replacing hydrogens on unsaturated carbon atoms in groups containing unsaturated carbons are, unless otherwise specified, —R$^{60}$, halo, —O$^-$M$^+$, —OR$^{70}$, —SR$^{70}$, —N(R$^{80}$)$_2$, perhaloalkyl, —CN, —OCN, —SCN, —NO, —NO$_2$, —N$_3$, —SO$_2$R$^{70}$, —SO$_3$$^-$M$^+$, —SO$_3$R$^{70}$, —OSO$_2$R$^{70}$, —OSO$_3$$^-$M$^+$, —OSO$_3$R$^{70}$, —PO$_3$$^{-2}$(M$^+$)$_2$, —PO$_3$$^{-2}$M$^{2+}$, —P(O)(OR$^{70}$)O$^-$M$^+$, —P(O)(OR$^{70}$)$_2$, —C(O)R$^{70}$, —C(S)R)$^{70}$, —C(NR$^{70}$)R$^{70}$, —CO$_2$$^-$M$^+$, —(CH$_2$)$_{1-3}$CO$_2$R$^{70}$, —CO$_2$R$^{70}$, —C(S)OR$^{70}$, —C(O)NR$^{80}$R$^{80}$, —C(NR$^{70}$)N(R$^{80}$)$_2$, —OC(O)R$^{70}$, —OC(S)R$^{70}$, —OCO$_2$$^-$M$^+$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$$^-$M$^+$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

Substituent groups for replacing hydrogens on nitrogen atoms in groups containing such nitrogen atoms are, unless otherwise specified, —R$^{60}$, —O$^-$M$^+$, —OR$^{70}$, —SR$^{70}$, —S$^-$M$^+$, —N(R$^{80}$)$_2$, perhaloalkyl, —CN, —NO, —NO$_2$, —S(O)$_2$R$^{70}$, —SO$_3$$^-$M$^+$, —SO$_3$R$^{70}$, —OS(O)$_2$R$^{70}$, —OSO$_3$$^-$M$^+$, —OSO$_3$R$^{70}$, —PO$_3$$^{2-}$(M)$_2$, —PO$_3$$^{2-}$M$^{2+}$, —P(O)(OR$^{70}$)O$^-$M$^+$, —P(O)(OR$^{70}$)(OR$^{70}$), —C(O)R$^{70}$, —C(S)R$^{70}$, —C(NR$^{70}$)R$^{70}$, —CO$_2$R$^{70}$, —C(S)OR$^{70}$, —C(O)NR$^8$OR$^{80}$, —C(NR$^{70}$)NR$^{80}$R$^{80}$, —OC(O)R$^{70}$, —OC(S)R$^{70}$, —OCO$_2$R$^{70}$, —OC(S)OR$^{70}$, —NR$^{70}$C(O)R$^{70}$, —NR$^{70}$C(S)R$^{70}$, —NR$^{70}$CO$_2$R$^{70}$, —NR$^{70}$C(S)OR$^{70}$, —NR$^{70}$C(O)N(R$^{80}$)$_2$, —NR$^{70}$C(NR$^{70}$)R$^{70}$ and —NR$^{70}$C(NR$^{70}$)N(R$^{80}$)$_2$, where R$^{60}$, R$^{70}$, R$^{80}$ and M$^+$ are as previously defined.

In one embodiment, a group that is substituted has 1, 2, 3, or 4 substituents, 1, 2, or 3 substituents, 1 or 2 substituents, or 1 substituent.

It is understood that in all substituted groups, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such case that the language permits such multiple substitutions, the maximum number of such iterations of substitution is three.

Similarly, it is understood that the above definitions are not intended to include impermissible substitution patterns (e.g., methyl substituted with 5 fluoro groups). Such impermissible substitution patterns are easily recognized by a person having ordinary skill in the art.

"Sulfonamide" refers to the group —SO$_2$NH$_2$, —N(H)SO$_2$H, —N(H)SO$_2$alkyl, —N(H)SO$_2$aryl, or —N(H)SO$_2$heterocyclyl.

"Sulfonyl" refers to the group —SO$_2$H, —SO$_2$alkyl, —SO$_2$aryl, or —SO$_2$heterocyclyl.

"Sulfanyl" refers to the group: —SH, —S-alkyl, —S-aryl, or —S-heterocyclyl.

"Sulfinyl" refers to the group: —S(O)H, —S(O)alkyl, —S(O)aryl or —S(O)heterocyclyl.

"Suitable leaving group" is defined as the term would be understood by one of ordinary skill in the art; that is, a group on a carbon, where upon reaction a new bond is to be formed, the carbon loses the group upon formation of the new bond. The invention pertains particularly with respect convergent synthesis, to reactions where such a leaving group is bonded to a reaction partner that is, e.g., aromatic, undergoes a bond-forming reaction and remains aromatic. A typical example is a nucleophilic substitution reaction, e.g., on a sp$^3$ hybridized carbon (SN$_2$ or SN$_1$), e.g. where the leaving group is a bromide, the reactant might be benzyl bromide. Another typical example of such a reaction is a nucleophilic aromatic substitution reaction (SNAr). Another example is an insertion reaction (for example by a transition metal) into the bond between an aromatic reaction partner bearing a leaving group followed by reductive coupling. "Suitable leaving group" is not limited to such mechanistic restrictions. Examples of suitable leaving groups include halogens, optionally substituted aryl or alkyl sulfonates, phosphonates, azides and —S(O)$_{0-2}$R where R is, for example optionally substituted alkyl, optionally substituted aryl, or optionally substituted heteroaryl.

"Stereoisomer" and "stereoisomers" refer to compounds that have the same atomic connectivity but different atomic arrangement in space. Stereoisomers include cis- and trans-isomers, E and Z isomers, enantiomers and diastereomers. Compounds of the invention, or their pharmaceutically acceptable salts can contain one or more asymmetric centers and can thus give rise to enantiomers, diastereomers, and other stereoisomeric forms that can be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers can be prepared using chiral synthons, chiral reagents, or resolved using conventional techniques, such as by: formation of diastereoisomeric salts or complexes which can be separated, for example, by crystallization; via formation of diastereoisomeric derivatives which can be separated, for example, by crystallization, selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. It will be appreciated that where a desired enantiomer is converted into another chemical entity by one of the separation procedures described above, a further step may be required to liberate the desired enantiomeric form. Alternatively, specific enantiomer can be synthesized by asymmetric synthesis using optically active reagents, substrates, catalysts or solvents, or by converting on enantiomer to the other by asymmetric transformation. For a mixture of enantiomers, enriched in a particular enantiomer, the major component enantiomer can be further enriched (with concomitant loss in yield) by recrystallization.

One of ordinary skill in the art will appreciate that compounds of the invention may exhibit the phenomena of tautomerism, conformational isomerism, geometric isomerism, and/or optical isomerism. For example, the compounds and prodrugs of the invention can include one or more chiral centers and/or double bonds and as a consequence can exist as stereoisomers, such as double-bond isomers (such as, geometric isomers), enantiomers, diastereomers, and mixtures thereof, such as racemic mixtures. As another example, the compounds of the invention can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, it would be understood that the invention encompasses any tautomeric, conformational isomeric, optical isomeric, and/or geometric isomeric forms of the compounds described herein, as well as mixtures of these various different isomeric forms. In cases of limited rotation, e.g. about a bond linking an aryl ring to the nitrogen in formula I, where Y is a bond, atropisomers are also possible and are also specifically included in the compounds of the invention. It is intended that the compounds encompassed herein are, with the exception of forms of isomerism, chemically stable and isolable.

When the compounds described herein contain olefinic double bonds or other centers of geometric asymmetry, and unless specified otherwise, it is intended that the compounds include both E and Z geometric isomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as benzimidazoles. A person of ordinary skill in the art would recognize that other tautomeric ring atom arrangements are possible and contemplated herein.

"Patient" or "Subject" refers to mammals and other animals, particularly humans. The methods are applicable to any subject capable of being infected with HIV-1. In one embodiment the patient or subject is a mammal. In another embodiment the patient or subject is a human.

"Co-administration" and/or "adjunctively" when used in reference to administration of a compound, pharmaceutical composition or both, with one or more other agents, indicates that the combination are administered such that there is some chronological overlap in their physiological activity on the organism or patient. Thus the HIV-1 fusion inhibitors described herein can be administered simultaneously and/or sequentially with one or more other agents.

"Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. Pharmaceutically acceptable acid addition salts are those salts that retain the biological effectiveness of the free bases while formed by acid partners that are not biologically or otherwise undesirable, e.g., inorganic acids such as hydrochloric acid, hydrobromic acid, sulfuric acid, nitric acid, phosphoric acid, and the like, as well as organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Pharmaceutically acceptable base addition salts include those derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic non-toxic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylamino ethanol, 2-diethyl amino ethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.)

"Pharmaceutically effective amount" and "therapeutically effective amount" refer to an amount of a compound sufficient to treat a specified disorder or disease or one or more of its symptoms and/or to prevent the occurrence of the disease or disorder. The amount of a compound which constitutes a "therapeutically effective amount" will vary depending on the compound, the disease state and its severity, the age of the patient to be treated, and the like. The therapeutically effective amount can be determined routinely by one of ordinary skill in the art.

"Prodrug" refers to compounds that are transformed in vivo to yield the parent compound, for example, by hydrolysis in the gut or enzymatic conversion in blood. Common examples include, but are not limited to, ester and amide forms of a compound having an active form bearing a carboxylic acid moiety. Examples of pharmaceutically acceptable esters of the compounds of this invention include, but are not limited to, alkyl esters (for example with between about one and about six carbons) where the alkyl group is a straight or branched chain. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of the compounds of the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Hoffman LaRoche, American Pharmaceutical Association and Pergamon Press, 1987, both of which are incorporated herein by reference for all purposes.

"Metabolite" refers to the break-down or end product of a compound or its salt produced by metabolism or biotransformation in the animal or human body; for example, biotransformation to a more polar molecule such as by oxidation, reduction, or hydrolysis, or to a conjugate (see Goodman and Gilman, "The Pharmacological Basis of Therapeutics" 8$^{th}$ Ed., Pergamon Press, Gilman et al. (eds), 1990 which is herein incorporated by reference). The metabolite of a compound described herein or its salt can itself be a biologically active compound in the body. While a prodrug described herein would meet this criteria, that is, from a described biologically active parent compound in vivo, "metabolite" is meant to encompass those compounds not contemplated to have lost a progroup, but rather all other compounds that are formed in vivo upon administration of a compound which retain the biological activities described herein. Thus one aspect is a metabolite of a compound described herein. For example, a biologically active metabolite is discovered serendipitously, that is, no prodrug design per se was undertaken. Stated another way, biologically active compounds inherently formed as a result of practicing methods of the invention, are themselves compounds of the invention. An assay for activity of a metabolite of a compound of the present invention is known to one of ordinary skill in the art.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. The compounds described herein can exist in unsolvated as well as solvated forms with solvents, pharmaceutically acceptable or not, such as water, ethanol, and the like. Solvated forms are encompassed by the invention, at least in generic terms.

"Treating" or "treatment" as used herein covers the treatment of the disease or condition of interest in a mammal, preferably a human, having the disease or condition of interest, and includes:

(i) preventing (i.e. prophylaxis) the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) stabilizing the disease or condition.

As used herein, the terms "disease" and "condition" can be used interchangeably or can be different in that the particular malady or condition may not have a known causative agent (so that etiology has not yet been worked out) and it is therefore not yet recognized as a disease but only as an undesirable condition or syndrome, where a more or less specific set of symptoms have been identified by clinicians.

Compounds and Compositions

Disclosed herein are novel compounds, methods of making the compounds, and methods of using these compounds in the treatment of conditions in which inhibiting HIV-1 fusion are therapeutically useful. The compounds find particular use in treating humans infected with HIV, alone or in combination with other agents. Given the severity and prevalence of HIV infection in humans, new therapies are needed.

One aspect of the invention is a compound of Formula I,

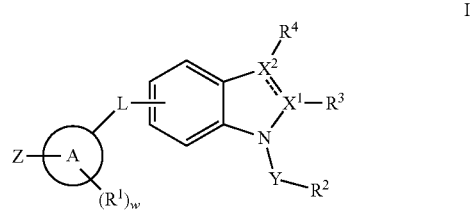

I or a pharmaceutically acceptable salt thereof, wherein:

A is a $C_{6-10}$aryl or a 5-15 membered heteroaryl;

L is a bond, —N(R$^a$)—, —O—, —S—, —S(O)—, —SO$_2$—, $C_{1-3}$alkylene or —OC$_{1-3}$alkylene;

Y is a bond or $C_{1-3}$alkylene;

Z is —CO$_2$R$^a$, —SO$_3$R$^a$, —OSO$_3$R$^a$, —PO$_3$R$^a$, —OPO$_3$R$^a$, —B(OR$^a$)$_2$, —OH, —S(O)$_2$N(H)—C(O)R$^a$, tetrazolyl, —C(O)N(R$^a$)—OH, —C(N═OH)—R$^a$ or H;

when Z is H, then at least one of R$^2$, R$^3$ or R$^4$ bears a group selected from —CO$_2$R$^a$, —SO$_3$R$^a$, —OSO$_3$R$^a$, —PO$_3$R$^a$, —OPO$_3$R$^a$, —B(OR$^a$)$_2$, —OH, —S(O)$_2$N(H)—C(O)R$^a$, tetrazolyl, —C(O)N(R$^a$)OH and —C(N═OH)—R$^a$;

when the bond between X$^1$ and X$^2$ is a single bond, X$^1$ and X$^2$ are independently CH or N, provided X$^1$ and X$^2$ are not simultaneously N;

when the bond between X$^1$ and X$^2$ is a double bond, X$^1$ and X$^2$ are independently C or N, provided X$^1$ and X$^2$ are not simultaneously N, and provided when either X$^1$ or X$^2$ is N, $R^3$ or $R^4$ is absent, respectively; that is, =N— can not bear a substitutent via a single bond, but quaternary salts are contemplated;

each $R^1$ is independently optionally substituted —$R^a$, halo, optionally substituted —$OR^a$, —O—$(C(R^a)_2)_m$—$OR^a$, $C_{1-3}$haloalkyloxy, —$SR^a$, —$N(R^c)_2$, —$CF_3$, —CN, —OCN, —SCN, —NO, —$NO_2$, —$N_3$, —$S(O)R^a$, —$S(O)_2R^a$, —$S(O)_2N(R^c)_2$, —$C(O)R^a$, —$C(O)N(R^c)_2$ or —$OC(O)R^a$;

each of $R^2$, $R^3$ and $R^4$ are, independently, —H, —$C(O)CO_2R^a$, —C(O)H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl;

each $R^a$ is independently H, $C_{1-6}$alkyl, $C_{3-8}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl;

each $R^c$ is independently $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;

each $R^d$ is =O, —$C_{1-6}$alkyl, —$OR^a$, —$OCF_3$, =S, —$SR^a$, =$NR^a$, =$NOR^a$, —$N(R^a)_2$, halo, —$CF_3$, —CN, —NC, —OCN, —SCN, —NO, —$NO_2$, =$N_2$, —$N_3$, —$S(O)R^a$, —$S(O)_2R^a$, —$SO_3R^a$, —$S(O)N(R^a)_2$, —$S(O)_2N(R^a)_2$, —$OS(O)R^a$, —$OS(O)_2R^a$, —$OSO_3R^a$, —$OS(O)_2N(R^a)_2$, —$C(O)R^a$, —$CO_2R^a$, —$C(O)N(R^a)_2$, —$C(NR^a)N(R^a)_2$, —$C(NOH)R^a$, —$C(NOH)N(R^a)_2$, —$OCO_2R^a$, —$OC(O)N(R^a)_2$, —$OC(NR^a)N(R^a)_2$, —$[N(R^a)C(O)]_nR^a$, —$(C(R^a)_2)_n$—$OR^a$, —$N(R^a)$—$S(O)_2R^a$, —C(O)—$C_{1-6}$haloalkyl, —$S(O)_2C_{1-6}$haloalkyl, —$OC(O)R^a$, —$O(C(R^a)_2)_m$—$OR^a$, —$S(C(R^a)_2)_m$—$OR^a$, —$N(R^a)C_{1-6}$haloalkyl, —$P(O)(OR^a)_2$, —$N(R^a)$—$(C(R^a)_2)_m$—$OR^a$, —$[N(R^a)C(O)]_nOR^a$, —$[N(R^a)C(O)]_nN(R^a)_2$, —$[N(R^a)C(NR^a)]_nN(R^a)_2$ or —$N(R^a)C(O)C_{1-6}$haloalkyl;

optionally two $R^d$, taken together with the atom or atoms to which they are attached, combine to form a 3-10 membered partially or fully saturated mono or bicyclic ring, optionally containing one or more heteroatoms and optionally substituted with one or more $R^a$;

w is 0, 1, 2, 3 or 4;
each m is 1, 2 or 3; and
each n is 0, 1, 2 or 3.

One embodiment is a compound of Formula I,

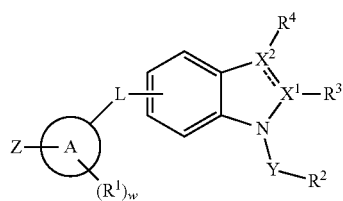

I or a pharmaceutically acceptable salt thereof, wherein:

A is a $C_{6-10}$aryl or a 5-15 membered heteroaryl;
L is a bond, —$N(R^a)$—, —O—, —S—, —S(O)—, —$SO_2$— or $C_{1-3}$alkylene;
Y is a bond or $C_{1-3}$alkylene;
Z is —$CO_2R^a$, —$SO_3R^a$, —$OSO_3R^a$, —$PO_3R^a$, —$OPO_3R^a$, —$B(OR^a)_2$, —OH, —$S(O)_2N(H)$—$C(O)R^a$, tetrazolyl, —$C(O)N(R^a)$—OH, —$C(N=OH)$—$R^a$ or H;

when Z is H, then at least one of $R^2$, $R^3$ or $R^4$ bears a group selected from —$CO_2R^a$, —$SO_3R^a$, —$OSO_3R^a$, —$PO_3R^a$, —$OPO_3R^a$, —$B(OR^a)_2$, —OH, —$S(O)_2N(H)$—$C(O)R^a$, tetrazolyl, —$C(O)N(R^a)OH$ and —$C(N=OH)$—$R^a$;

when the bond between $X^1$ and $X^2$ is a single bond, $X^1$ and $X^2$ are independently CH or N, provided $X^1$ and $X^2$ are not simultaneously N;

when the bond between $X^1$ and $X^2$ is a double bond, $X^1$ and $X^2$ are independently C or N, provided $X^1$ and $X^2$ are not simultaneously N and provided, when $X^1$ or $X^2$ is N, then $R^3$ or $R^4$ is absent, respectively;

each $R^1$ is independently —$R^a$, halo, —$OR^a$, —O—(C$(R^a)_2)_m$—$OR^a$, $C_{1-3}$haloalkyloxy, —$SR^a$, —$N(R^c)_2$, —$CF_3$, —CN, —OCN, —SCN, —NO, —$NO_2$, —$N_3$, —$S(O)R^a$, —$S(O)_2R^a$, —$S(O)_2N(R^c)_2$, —$C(O)R^a$, —$C(O)N(R^c)_2$ or —$OC(O)R^a$;

each of $R^2$, $R^3$ and $R^4$ are, independently, —H, —$C(O)CO_2R^a$, —C(O)H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl;

each $R^a$ is independently H, $C_{1-6}$alkyl, $C_{3-8}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl;

each $R^c$ is independently $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;

each $R^d$ is =O, —$C_{1-6}$alkyl, —$OR^a$, —$OCF_3$, =S, —$SR^a$, =$NR^a$, =$NOR^a$, —$N(R^a)_2$, halo, —$CF_3$, —CN, —NC, —OCN, —SCN, —NO, —$NO_2$, =$N_2$, —$N_3$, —$S(O)R^a$, —$S(O)_2R^a$, —$SO_3R^a$, —$S(O)N(R^a)_2$, —$S(O)_2N(R^a)_2$, —$OS(O)R^a$, —$OS(O)_2R^a$, —$OSO_3R^a$, —$OS(O)_2N(R^a)_2$, —$C(O)R^a$, —$CO_2R^a$, —$C(O)N(R^a)_2$, —$C(NR^a)N(R^a)_2$, —$C(NOH)R^a$, —$C(NOH)N(R^a)_2$, —$OCO_2R^a$, —$OC(O)N(R^a)_2$, —$OC(NR^a)N(R^a)_2$, —$[N(R^a)C(O)]_nR^a$, —$(C(R^a)_2)_n$—$OR^a$, —$N(R^a)$—$S(O)_2R^a$, —C(O)—$C_{1-6}$haloalkyl, —$S(O)_2C_{1-6}$haloalkyl, —$OC(O)R^a$, —$O(C(R^a)_2)_m$—$OR^a$, —$S(C(R^a)_2)_m$—$OR^a$, —$N(R^a)C_{1-6}$halo alkyl, —$P(O)(OR^a)_2$, —$N(R^a)$—$(C(R^a)_2)_m$—$OR^a$, —$[N(R^a)C(O)]_n$—$OR^a$, —$[N(R^a)C(O)]_nN(R^a)_2$, —$[N(R^a)C(NR^a)]_nN(R^a)_2$ or —$N(R^a)C(O)C_{1-6}$haloalkyl;

optionally two $R^d$, taken together with the atom or atoms to which they are attached, combine to form a 3-10 membered partially or fully saturated mono or bicyclic ring, optionally containing one or more heteroatoms and optionally substituted with one or more $R^a$;

w is 0, 1, 2, 3 or 4;

each m is 1, 2 or 3; and each n is 0, 1, 2 or 3.

In one embodiment, A is selected from the group consisting of phenyl, pyridyl, pyrimidinyl, pyrazinyl, indolyl, indolinyl, isoindolinyl, benzimidazolyl, indazolyl, quinolyl, napthalenyl, isoquinolyl and quinazolinyl. In this embodiment, the bicyclic ring system including $X^1$ and $X^2$ is an indole, a benzimidazole, an indazole or an indoline. In one embodiment, where A is benzimidazolyl, indolyl, isoindolinyl or indazolyl, the group L is attached to the benzimidazolyl, indolyl, isoindolinyl or indazolyl at the 5- or 6-position or at a nitrogen of the benzimidazolyl, indolyl, isoindolinyl or indazolyl. In one embodiment, where A is quinolyl or quinazolinyl, the group L is attached to the quinolyl or quinazolinyl at the 2-position. In one embodiment, L is a bond, —$CH_2$—, —O— or —$OC_{1-3}$alkylene. In one embodiment, where an $R^1$ is a substituted —$R^a$, the substitution on $R^a$ is selected from —$CO_2R^e$, —$SO_3R^e$, —$OSO_3R^e$, —$PO_3R^e$, —$OPO_3R^e$, —$B(OR^e)_2$, —$OR^e$, —$S(O)_2N(H)$—$C(O)R^e$, tetrazolyl, —$C(O)N(R^e)OH$ and —$C(N=OH)$—$R^e$, where $R^e$ is H, $C_{1-6}$alkyl, $C_{3-8}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl.

In one embodiment, the ring bearing $X^1$ and $X^2$ is an indole substituted at various positions with one or more substituted aryl groups, arylalkyl groups, heteroaryl groups and/or heteroarylalkyl groups. More specifically, indoles substituted at various positions with one or more optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl and/or 6-16 membered heteroarylalkyl groups. Optional substitution may vary according to that described above in relation to replacing one or more hydrogens on saturated carbons, unsaturated carbons and/or nitrogens.

One embodiment is a compound of structural Formula I where ring A is a phenyl substituted with various groups. In one embodiment, the compound is according to Formula II,

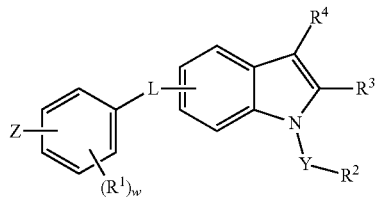

II where the remaining variables are defined in the same way as for the those of Formula I. One embodiment is a compound of Formula II where L is a bond, $C_{1-3}$alkylene, —O— or —$OC_{1-3}$ alkylene. In a more specific embodiment, in accord with the previous embodiment where L is a bond, $C_{1-3}$alkylene, —O— or —$OC_{1-3}$alkylene, Z is —$CO_2R^a$, —$SO_3R^a$, —$PO_3R^a$, —$S(O)_2N(H)$—$C(O)R^a$, tetrazolyl, —$C(O)N(R^a)$—OH or H; when Z is H, then at least one of $R^2$, $R^3$ or $R^4$ bears a group —$CO_2R^a$, —$SO_3R^a$, —$PO_3R^a$, —$S(O)_2N(H)$—$C(O)R^a$, tetrazolyl or —$C(O)N(R^a)$—OH; each of $R^2$, $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl; and each $R^d$ is =O, —$OR^a$, —$OCF_3$, —$SR^a$, =$NR^a$, =$NOR^a$, —$N(R^a)_2$, halo, —$CF_3$, —CN, —NO, —$NO_2$, =$N_2$, —$N_3$, —$S(O)R^a$, —$S(O)_2R^a$, —$SO_3R^a$, —$S(O)N(R^a)_2$, —$S(O)_2N(R^a)_2$, —$OSO_3R^a$, —$C(O)R^a$, —$CO_2R^a$, —$C(O)N(R^a)_2$, —$(CH_2)_n$—$OR^a$, —$N(H)$—$S(O)_2R^a$, —$C(O)$—$C_{1-6}$haloalkyl, —$S(O)_2C_{1-6}$haloalkyl, —$OC(O)R^a$, —$O(CH_2)_m$—$OR^a$, —$S(CH_2)_m$—$OR^a$, —$NHC_{1-6}$haloalkyl, —$N(R^a)$—$(CH_2)_m$—$OR^a$, —[N(H)C(O)]$_n$$OR^a$ or —$N(R^a)C(O)C_{1-6}$haloalkyl. In a more specific embodiment, in accord with the previous embodiment, L is $C_{1-3}$alkylene or —$OC_{1-3}$alkylene. In another embodiment, in accord with the previous embodiment, L is $C_{1-2}$alkylene or —$OCH_2$—. In another embodiment, in accord with the previous embodiment, L is $C_{1-2}$alkylene. In another embodiment, in accord with the previous embodiment, L is —$CH_2$—.

Another embodiment is a compound of Formula II, more specifically according to Formula IIa,

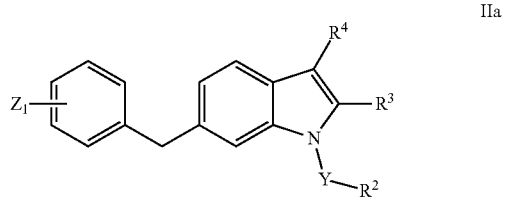

IIa where $Z_1$ is —$CO_2R^a$, —$SO_3R^a$, —$PO_3R^a$ or H; and, when $Z_1$ is H, then at least one of $R^2$, $R^3$ or $R^4$ bears a group —$CO_2R^a$, —$SO_3R^a$ or —$PO_3R^a$. In a more specific embodiment, $Z_1$ is —$CO_2H$ and Y is $C_{1-3}$alkylene. In a more specific embodiment, in accord with the previous embodiment where, $Z_1$ is —$CO_2H$ and Y is $C_{1-3}$alkylene, $R^2$ is optionally substituted $C_{6-10}$aryl or optionally substituted 5-15 membered heteroaryl; and each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl. In a more specific embodiment, $R^2$ is optionally substituted phenyl or optionally substituted indolyl. In one embodiment, $R^2$ is phenyl optionally substituted with up to three groups, each independently selected from optionally substituted $C_{1-6}$alkyl, halo, —$OC_{1-6}$alkyl, —$N(C_{1-6}$alkyl)$_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$alkyl)$_2$. In another embodiment, $R^2$ is indol-1-yl, indol-2-yl or indol-3-yl, optionally substituted with up to three groups, each independently selected from optionally substituted $C_{1-6}$alkyl, optionally substituted benzyl, halo, —$OC_{1-6}$alkyl, —$N(C_{1-6}$alkyl)$_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$alkyl)$_2$.

Another embodiment is a compound according to Formula IIa, where $Z_1$ is —$CO_2H$ and Y is a bond. In one embodiment, where $Z_1$ is —$CO_2H$ and Y is a bond, $R^2$ is H or optionally substituted $C_{6-10}$aryl; and each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl. In a more specific embodiment, $R^2$ is H or optionally substituted phenyl. In one embodiment $R^2$ is phenyl optionally substituted with up to three groups, each independently selected from optionally substituted $C_{1-6}$alkyl, halo, —$OC_{1-6}$alkyl, —OH, —$N(C_{1-6}$ alkyl)$_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$alkyl)$_2$. In another embodiment $R^2$ is H.

Another embodiment is a compound of Formula II, more specifically according to Formula IIb,

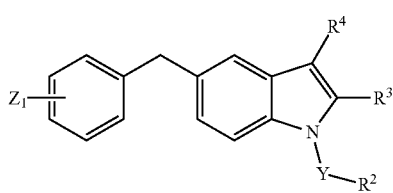

IIb where $Z_1$ is —$CO_2R^a$, —$SO_3R^a$, —$PO_3R^a$ or H; and when $Z_1$ is H, then at least one of $R^2$, $R^3$ or $R^4$ bears a group —$CO_2R^a$, —$SO_3R^a$ or —$PO_3R^a$. In one embodiment $Z_1$ is —$CO_2H$ and Y is $C_{1-3}$alkylene. In one embodiment, where $Z_1$ is —$CO_2H$ and Y is $C_{1-3}$alkylene, $R^2$ is optionally substituted $C_{6-10}$aryl or optionally substituted 5-15 membered heteroaryl; and each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl. In a more specific embodiment $R^2$ is optionally substituted phenyl or optionally substituted indolyl. In one embodiment $R^2$ is phenyl optionally substituted with up to three groups, each independently selected from optionally substituted $C_{1-6}$alkyl, halo, —$OC_{1-6}$alkyl, —OH, —$N(C_{1-6}$alkyl)$_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)$ $C_{1-6}$alkyl and —$C(O)N(C_{1-6}$alkyl)$_2$. In another embodiment $R^2$ is indol-1-yl, indol-2-yl or indol-3-yl, optionally substituted with up to three groups, each independently selected from optionally substituted $C_{1-6}$alkyl, optionally substituted benzyl, halo, —$OC_{1-6}$alkyl, —OH, —$N(C_{1-6}$alkyl)$_2$, —$N(H)$ $C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$alkyl)$_2$.

Another embodiment is a compound according to Formula IIb, where $Z_1$ is —$CO_2H$ and Y is a bond. In one embodiment, where $Z_1$ is —$CO_2H$ and Y is a bond, $R^2$ is H or optionally substituted $C_{6-10}$aryl; and each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl. In a more specific embodiment, $R^2$ is H or optionally substituted phenyl. In one embodiment $R^2$ is phenyl optionally substituted with up to three groups, each independently selected from optionally substituted $C_{1-6}$alkyl, halo, —$OC_{1-6}$alkyl, —OH, —$N(C_{1-6}$ alkyl)$_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$alkyl)$_2$. In another embodiment $R^2$ is H.

Another embodiment is a compound according to Formula II, where L is a bond. One such embodiment is a compound according to Formula IIc,

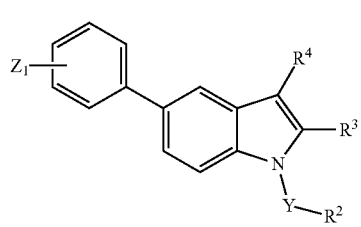

IIc where $Z_1$ is —$CO_2R^a$, —$SO_3R^a$, —$PO_3R^a$ or H; and when $Z_1$ is H, then at least one of $R^2$, $R^3$ or $R^4$ bears a group —$CO_2R^a$, —$SO_3R^a$ or —$PO_3R^a$. In one embodiment $Z_1$ is —$CO_2H$ and Y is $C_{1-3}$alkylene. In one embodiment, where $Z_1$ is —$CO_2H$ and Y is $C_{1-3}$alkylene, $R^2$ is optionally substituted $C_{6-10}$aryl or optionally substituted 5-15 membered heteroaryl; and each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl. In a more specific embodiment $R^2$ is optionally substituted phenyl or optionally substituted indolyl. In one embodiment $R^2$ is phenyl optionally substituted with up to three groups, each independently selected from optionally substituted $C_{1-6}$alkyl, halo, —$OC_{1-6}$alkyl, —OH, —$N(C_{1-6}$alkyl)$_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)$ $C_{1-6}$alkyl and —$C(O)N(C_{1-6}$alkyl)$_2$. In another embodiment $R^2$ is indol-1-yl, indol-2-yl or indol-3-yl, optionally substituted with up to three groups, each independently selected from optionally substituted $C_{1-6}$alkyl, optionally substituted benzyl, halo, —$OC_{1-6}$alkyl, —OH, —$N(C_{1-6}$alkyl)$_2$, —$N(H)$ $C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$ alkyl)$_2$.

Another embodiment is a compound according to Formula IIc, where $Z_1$ is —$CO_2H$ and Y is a bond. In one embodiment, where $Z_1$ is —$CO_2H$ and Y is a bond, $R^2$ is H or optionally substituted $C_{6-10}$aryl; and each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl. In a more specific embodiment, $R^2$ is H or optionally substituted phenyl. In one embodiment $R^2$ is phenyl optionally substituted with up to three groups, each independently selected from optionally substituted $C_{1-6}$alkyl, halo, —$OC_{1-6}$alkyl, —OH, —$N(C_{1-6}$ alkyl)$_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$alkyl)$_2$. In another embodiment $R^2$ is H.

Another embodiment is a compound according to Formula II, where L is a bond. One embodiment is a compound according to Formula IId,

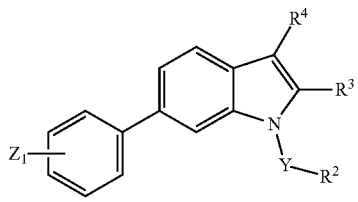

where $Z_1$ is —$CO_2R^a$, —$SO_3R^a$, —$PO_3R^a$ or H; and when $Z_1$ is H, then at least one of $R^2$, $R^3$ or $R^4$ bears a group —$CO_2R^a$, —$SO_3R^a$ or —$PO_3R^a$. In one embodiment $Z_1$ is —$CO_2H$ and Y is $C_{1-3}$alkylene. In one embodiment, where $Z_1$ is —$CO_2H$ and Y is $C_{1-3}$alkylene, $R^2$ is optionally substituted $C_{6-10}$aryl or optionally substituted 5-15 membered heteroaryl; and each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl. In a more specific embodiment $R^2$ is optionally substituted phenyl or optionally substituted indolyl. In one embodiment $R^2$ is phenyl optionally substituted with up to three groups, each independently selected from optionally substituted $C_{1-6}$alkyl, halo, —$OC_{1-6}$alkyl, —OH, —$N(C_{1-6}$alkyl$)_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$alkyl$)_2$.

In another embodiment $R^2$ is indol-1-yl, indol-2-yl or indol-3-yl, optionally substituted with up to three groups, each independently selected from optionally substituted $C_{1-6}$alkyl, optionally substituted benzyl, halo, —$OC_{1-6}$alkyl, —OH, —$N(C_{1-6}$alkyl$)_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$alkyl$)_2$.

Another embodiment is a compound according to Formula IId, where $Z_1$ is —$CO_2H$ and Y is a bond. In one embodiment, where $Z_1$ is —$CO_2H$ and Y is a bond, $R^2$ is H or optionally substituted $C_{6-10}$aryl; and each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl. In a more specific embodiment, $R^2$ is H or optionally substituted phenyl. In one embodiment $R^2$ is phenyl optionally substituted with up to three groups, each independently selected from optionally substituted $C_{1-6}$alkyl, halo, —$OC_{1-6}$alkyl, —OH, —$N(C_{1-6}$alkyl$)_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl and —$C(O)N(C_{1-6}$alkyl$)_2$. In another embodiment $R^2$ is H.

One embodiment is a compound of structural Formula I where ring A is an aromatic ring substituted with various groups. In one embodiment Y is $C_{1-3}$alkylene and L is a bond or Y is a bond and L is —$N(R^a)$—, —O—, —S—, —S(O)—, —$SO_2$— or $C_{1-3}$alkylene. In a more specific embodiment, A is selected from the group consisting of phenyl, pyridyl, pyrimidinyl, pyrazinyl, indolyl, benzimidazolyl, indazolyl, quinolyl, napthalenyl, isoquinolyl and quinazolinyl. In another embodiment, A is a phenyl, and the compound, or a pharmaceutically acceptable salt thereof, is according to Formula IIIa or IIIb,

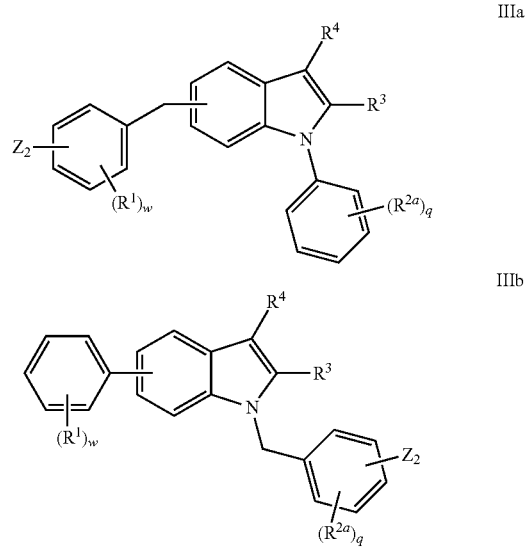

where:
$Z_2$ is —$CO_2R^a$;
each $R^1$ is independently —$R^a$, halo, —$OR^a$, —O—$(CR^a)_2)_m$—$OR^a$, $C_{1-3}$haloalkyloxy, —$SR^a$, —$N(R^c)_2$, —$CF_3$, —CN, —OCN, —SCN, —NO, —$NO_2$, —$N_3$, —$S(O)R^a$, —$S(O)_2R^a$, —$S(O)_2N(R^c)_2$, —$C(O)R^a$, —$C(O)N(R^c)_2$ or —$OC(O)R^a$;
each $R^{2a}$ is independently optionally substituted $C_{1-6}$alkyl, halo, —$OC_{1-6}$alkyl, —OH, —$N(C_{1-6}$alkyl$)_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl or —$C(O)N(C_{1-6}$alkyl$)_2$;
each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl;
each $R^a$ is independently H, $C_{1-6}$alkyl, $C_{3-8}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl;
each $R^c$ is independently $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;
each $R^d$ is =O, —$OR^a$, —$OCF_3$, —$SR^a$, =$NR^a$, =$NOR^a$, —$N(R^a)_2$, halo, —$CF_3$, —CN, —NO, —$NO_2$, =$N_2$, —$N_3$, —$S(O)R^a$, —$S(O)_2R^a$, —$SO_3R^a$, —$S(O)N(R^a)_2$, —$S(O)_2N(R^a)_2$, —$OSO_3R^a$, —$C(O)R^a$, —$CO_2R^a$, —$C(O)N(R^a)_2$, —$(CH_2)_n$—$OR^a$, —$N(H)$—$S(O)_2R^a$, —$C(O)$—$C_{1-6}$haloalkyl, —$S(O)_2C_{1-6}$haloalkyl, —$OC(O)R^a$, —$O(CH_2)_n$—$OR^a$, —$S(CH_2)_n$—$OR^a$, —NHC$_{1-6}$ haloalkyl, —N(R$^a$)—(CH$_2$)$_n$—OR$^a$, —[N(H)C(O)]$_n$OR$^a$ or —N(R$^a$)C(O)C$_{1-6}$haloalkyl.

optionally two R$^d$, taken together with the atom or atoms to which they are attached, combine to form a 3-10 membered partially or fully saturated mono or bicyclic ring, optionally containing one or more heteroatoms and optionally substituted with one or more R$^a$;

w is 0, 1, 2, 3 or 4;

q is 0, 1, 2, 3, 4 or 5;

each m is 1, 2 or 3; and each n is 0, 1, 2 or 3.

One embodiment is a compound of Formula IIIa where at least one of R$^{2a}$ is —OC$_{1-3}$alkyl. Another embodiment is a compound of Formula IIIb where at least one of R$^1$ is —OC$_{1-3}$alkyl. Another embodiment is a compound according either of the previous two embodiments where Z$_2$ is —CO$_2$H or a pharmaceutically acceptable salt thereof. Yet another embodiment is a compound according to the previous embodiment where each of R$^3$ and R$^4$ are, independently, —H, halo, optionally substituted C$_{1-6}$alkyl or optionally substituted phenyl. Another embodiment is a compound of Formula IIIa where at least one of R$^{2a}$ is —OCH$_3$. Another embodiment is a compound of Formula nib where at least one of R$^1$ is —OCH$_3$. In another embodiment, a compound of Formula IIIa bears two or three of R$^{2a}$ that are —OCH$_3$. In another embodiment, a compound of Formula IIIb bears two or three of R$^1$ that are —OCH$_3$.

One embodiment, where ring A is a phenyl, L is a bond, Y is —CH$_2$— and R$^2$ is optionally substituted phenyl, is a compound of formula IV:

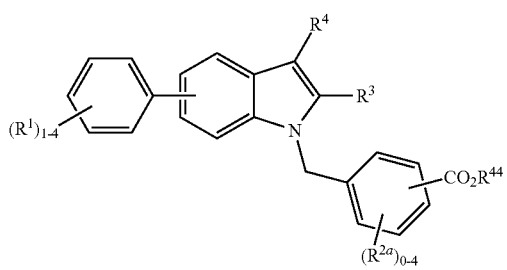

IV or a pharmaceutically acceptable salt thereof, wherein:

each R$^1$ is independently optionally substituted —R$^a$, halo, optionally substituted —OR$^a$, —O—(C(R$^a$)$_2$)$_m$—OR$^a$, C$_{1-3}$haloalkyloxy, —SR$^a$, —N(R$^c$)$_2$, —CF$_3$, —CN, —NO$_2$, —S(O)$_2$R$^a$, —S(O)$_2$N(R$^c$)$_2$, —C(O)R$^a$, —C(O)N(R$^c$)$_2$ or —OC(O)R$^a$;

each R$^{2a}$ is independently optionally substituted C$_{1-6}$alkyl, halo, —OC$_{1-6}$alkyl, —OH, —N(C$_{1-6}$alkyl)$_2$, —N(H)C$_{1-6}$alkyl, —CN, —NO$_2$, —C(O)C$_{1-6}$alkyl, —CO$_2$H, —CO$_2$C$_{1-6}$alkyl, —C(O)N(H)C$_{1-6}$alkyl or —C(O)N(C$_{1-6}$alkyl)$_2$;

each of R$^3$ and R$^4$ are, independently, —H, —C(O)CO$_2$R$^a$, —C(O)H, halo, optionally substituted C$_{1-6}$alkyl, optionally substituted C$_{3-8}$cycloalkyl, optionally substituted C$_{4-11}$cycloalkylalkyl, optionally substituted C$_{6-10}$aryl, optionally substituted C$_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl;

each R$^a$ is independently H, C$_{1-6}$alkyl, C$_{3-8}$cycloalkyl, C$_{4-11}$cycloalkylalkyl, C$_{6-10}$aryl, C$_{7-16}$arylalkyl, 3-10 membered heteroalicyclyl, 4-11 membered heteroalicyclylalkyl, 5-15 membered heteroaryl or 6-16 membered heteroarylalkyl;

each R$^c$ is independently R$^a$, or, alternatively, two R$^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different R$^a$ and/or R$^d$ groups;

each R$^d$ is =O, —C$_{1-6}$alkyl, —OR$^a$, —OCF$_3$, =S, —SR$^a$, =NR$^a$, =NOR$^a$, —N(R$^a$)$_2$, halo, —CF$_3$, —CN, —NC, —OCN, —SCN, —NO, —NO$_2$, =N$_2$, —N$_3$, —S(O)R$^a$, —S(O)$_2$R$^a$, —SO$_3$R$^a$, —S(O)N(R$^a$)$_2$, —S(O)$_2$N(R$^a$)$_2$, —OS(O)R$^a$, —OS(O)$_2$R$^a$, —OSO$_3$R$^a$, —OS(O)$_2$N(R$^a$)$_2$, —C(O)R$^a$, —CO$_2$R$^a$, —C(O)N(R$^a$)$_2$, —C(NR$^a$)N(R$^a$)$_2$, —C(NOH)R$^a$, —C(NOH)N(R$^a$)$_2$, —OCO$_2$R$^a$, —OC(O)N(R$^a$)$_2$, —OC(NR$^a$)N(R$^a$)$_2$, —[N(R$^a$)C(O)]$_n$R$^a$, —(C(R$^a$)$_2$)$_n$—OR$^a$, —N(R$^a$)—S(O)$_2$R$^a$, —C(O)—C$_{1-6}$haloalkyl, —S(O)$_2$C$_{1-6}$haloalkyl, —OC(O)R$^a$, —O(C(R$^a$)$_2$)$_m$—OR$^a$, —S(C(R$^a$)$_2$)$_m$—OR$^a$, —N(R$^a$)C$_{1-6}$halo alkyl, —P(O)(OR$^a$)$_2$, —N(R$^a$)—(C(R$^a$)$_2$)$_m$—OR$^a$, —[N(R$^a$)C(O)]$_n$OR$^a$, —[N(R$^a$)C(O)]$_n$N(R$^a$)$_2$, —[N(R$^a$)C(NR$^a$)]$_n$N(R$^a$)$_2$ or —N(R$^a$)C(O)C$_{1-6}$haloalkyl;

optionally two R$^d$, taken together with the atom or atoms to which they are attached, combine to form a 3-10 membered partially or fully saturated mono or bicyclic ring, optionally containing one or more heteroatoms and optionally substituted with one or more R$^a$;

R$^{44}$ is optionally substituted R$^a$ or a carboxylic acid counter ion;

each m is 1, 2 or 3; and each n is 0, 1, 2 or 3.

As described above, one embodiment is a compound of formula I where at least one of R$^1$ is optionally substituted —OR$^a$, where Z is H or non-H. In one such embodiment, where Z is H and there is one —OR$^a$, the —OR$^a$ is an optionally substituted benzyloxy group. In accord with the previous embodiment, one embodiment is where A is an optionally substituted phenylene. In one embodiment, the compound in accord with formula IV, more specifically according to formula IVa:

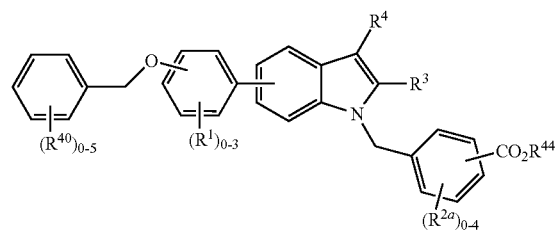

IVa wherein:

each R$^{40}$ is independently R$^{60a}$, halo, —OR$^{70a}$, —SR$^{70a}$, —N(R$^{80a}$)$_2$, perhaloalkyl, —CN, —NO$_2$, —SO$_2$R$^{70a}$, —SO$_3$R$^{70a}$, —OSO$_3$R$^{70a}$, —C(O)R$^{70a}$, —CO$_2$R$^{70a}$, —C(O)NR$^{80a}$R$^{80a}$, —NR$^{70a}$C(O)R$^{70a}$, —NR$^a$CO$_2$R$^{70a}$ and —NR$^{70a}$C(O)N(R$^{80a}$)$_2$, where R$^{60a}$ is C$_{1-6}$alkyl; each R$^{70a}$ is independently hydrogen or R$^{60a}$; each R$^{80a}$ is independently R$^{70a}$ or alternatively, two R$^{80a}$'s, taken together with the nitrogen atom to which they are bonded, form a 3 to 7-membered heteroalicyclyl which optionally includes from 1 to 4 of the same or different additional heteroatoms selected from O, N and S, of which N optionally has H or $C_1$-$C_3$alkyl substitution;

each $R^1$ is independently halo, $C_{1-6}$alkyl, optionally substituted —$OR^a$, —O—$(C(R^a)_2)_m$—$OR^a$, $C_{1-3}$haloalkyloxy, —$SR^a$, —$N(R^c)_2$, —$CF_3$, —CN, —$NO_2$, —$S(O)_2R^a$, —$S(O)_2N(R^c)_2$, —$C(O)R^a$, —$C(O)N(R^c)_2$ or —OC(O)$R^a$;

each $R^{2a}$ is independently optionally substituted $C_{1-6}$alkyl, halo, —$OC_{1-6}$alkyl, —OH, —$N(C_{1-6}$alkyl$)_2$, —N(H)$C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$ alkyl or —$C(O)N(C_{1-6}$alkyl$)_2$;

each of $R^3$ and $R^4$ are, independently, —H, halo, optionally substituted $C_{1-6}$alkyl, optionally substituted $C_{6-10}$aryl, optionally substituted $C_{7-16}$arylalkyl, optionally substituted 3-10 membered heteroalicyclyl, optionally substituted 4-11 membered heteroalicylylalkyl, optionally substituted 5-15 membered heteroaryl or 6-16 membered heteroarylalkyl;

each $R^a$ is independently H, $C_{1-6}$alkyl, $C_{3-8}$cycloalkyl, $C_{4-11}$cycloalkylalkyl, $C_{6-10}$aryl, $C_{7-16}$arylalkyl, 3-10 membered heteroalicyclyl, 4-11 membered heteroalicylylalkyl, 5-15 membered heteroaryl or 6-16 membered heteroarylalkyl;

each $R^c$ is independently $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;

each $R^d$ is =O, —$C_{1-6}$alkyl, —$OR^a$, —$OCF_3$, =S, —$SR^a$, =$NR^a$, =$NOR^a$, —$N(R^a)_2$, halo, —$CF_3$, —CN, —NC, —OCN, —SCN, —NO, —$NO_2$, =$N_2$, —$N_3$, —$S(O)R^a$, —$S(O)_2R^a$, —$SO_3R^a$, —$S(O)N(R^a)_2$, —$S(O)_2N(R^a)_2$, —$OS(O)R^a$, —$OS(O)_2R^a$, —$OSO_3R^a$, —$OS(O)_2N(R^a)_2$, —$C(O)R^a$, —$CO_2R^a$, —$C(O)N(R^a)_2$, —$C(NR^a)N(R^a)_2$, —$C(NOH)R^a$, —$C(NOH)N(R^a)_2$, —$OCO_2R^a$, —$OC(O)N(R^a)_2$, —$OC(NR^a)N(R^a)_2$, —[$N(R^a)C(O)]_nR^a$, —$(C(R^a)_2)_n$—$OR^a$, —$N(R^a)$—$S(O)_2R^a$, —$C(O)$—$C_{1-6}$haloalkyl, —$S(O)_2C_{1-6}$haloalkyl, —$OC(O)R^a$, —$O(C(R^a)_2)_m$—$OR^a$, —$S(C(R^a)_2)_m$—$OR^a$, —$N(R^a)C_{1-6}$halo alkyl, —$P(O)(OR^a)_2$, —$N(R^a)$—$(C(R^a)_2)_m$—$OR^a$, —[$N(R^a)C(O)]_nOR^a$, —[$N(R^a)C(O)]_nN(R^a)_2$, —[$N(R^a)C(NR^a)]_nN(R^a)_2$ or —$N(R^a)C(O)C_{1-6}$haloalkyl;

optionally two $R^d$, taken together with the atom or atoms to which they are attached, combine to form a 3-10 membered partially or fully saturated mono or bicyclic ring, optionally containing one or more heteroatoms and optionally substituted with one or more $R^a$;

$R^{44}$ is optionally substituted $R^a$ or a carboxylic acid counter ion;

each m is 1, 2 or 3; and
each n is 0, 1, 2 or 3.

As described above, one embodiment is a compound of formula I where at least one of $R^1$ is optionally substituted —$OR^a$, where Z is H or non-H. In one such embodiment, where Z is H and there is one —$OR^a$, the —$OR^a$ is an optionally substituted benzyloxy group. In accord with the previous embodiment, one embodiment is where A is an optionally substituted phenylene. In one such embodiment, the compound is in accord with formula IVa, more specifically according to formula IVb:

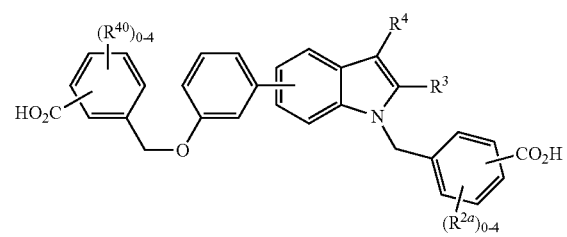

IVb where each $R^{40}$ is independently $C_{1-6}$alkyl, halo, —$OC_{1-6}$alkyl, —OH, —$N(R^{80a})_2$, perhaloalkyl, —CN, —$NO_2$, —$CO_2C_{1-6}$alkyl or —$C(O)NR^{80a}R^{80a}$, where each $R^{80a}$ is independently H or $C_{1-6}$alkyl; each $R^{2a}$ is independently optionally substituted $C_{1-6}$alkyl, halo, —$OC_{1-6}$alkyl, —OH, —$N(C_{1-6}$alkyl$)_2$, —N(H)$C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl or —$C(O)N(C_{1-6}$alkyl$)_2$; and each of $R^3$ and $R^4$ are, independently, —H, halo or $C_{1-6}$alkyl.

In one embodiment, the compound is according to formula IVb, having formula IVbi:

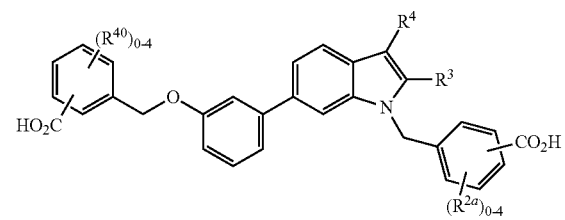

IVbi

In one embodiment, the compound is according to formula IVbi and each of the distal carboxylic acid groups are, independently, either meta or para to the benzyl methylene.

In one embodiment, the compound in accord with formula IVa, more specifically according to formula IVc:

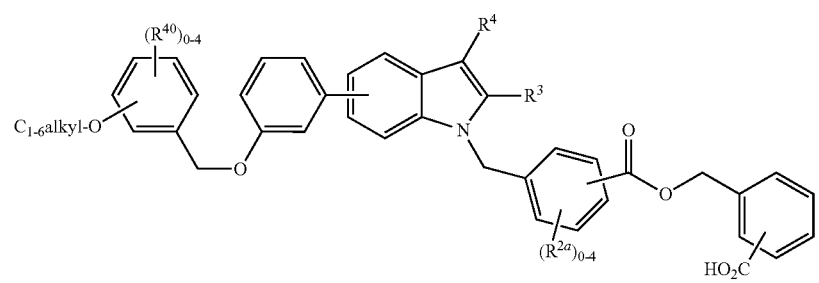

IVc where each $R^{40}$ is independently $C_{1-6}$alkyl, halo, —$OC_{1-6}$alkyl, —OH, —$N(R^{80a})_2$, perhaloalkyl, —CN, —$NO_2$, —$CO_2C_{1-6}$alkyl or —$C(O)NR^{80a}R^{80a}$, where each $R^{80a}$ is independently H or $C_{1-6}$alkyl; each $R^{2a}$ is independently optionally substituted $C_{1-6}$alkyl, halo, —$OC_{1-6}$alkyl, —OH, —$N(C_{1-6}$alkyl$)_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl or —$C(O)N(C_{1-6}$alkyl$)_2$; and each of $R^3$ and $R^4$ are, independently, —H, halo or $C_{1-6}$alkyl.

In one embodiment, the compound is according to formula IVc, having formula IVci:

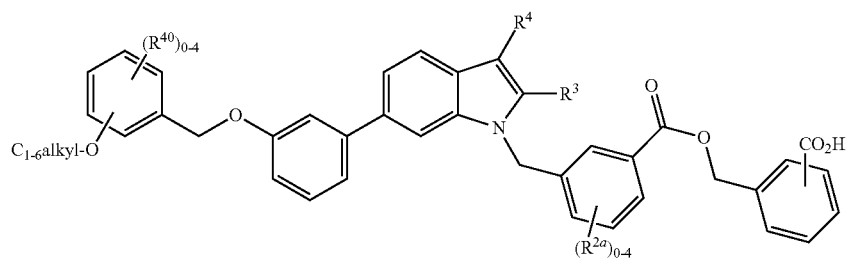

IVci

In one embodiment, the compound is according to formula IVci and each of the distal carboxylic acid group is either meta or para to the benzyl methylene and the distal $C_{1-6}$alkylO-group is para to the corresponding benzyl methylene. In one embodiment the $C_{1-6}$alkylO-group is a methoxy or ethoxy group.

One embodiment is a compound of formula V:

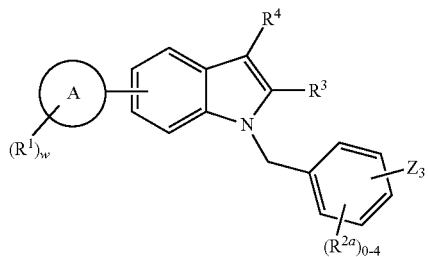

V or a pharmaceutically acceptable salt thereof, wherein:
A is a 5-15 membered heteroaryl;
$Z_3$ is —$(CH_2)_{0-3}CO_2R^a$ or H
each $R^1$ is independently optionally substituted —$R^a$, halo, —$OR^a$, —O—$(C(R^a)_2)_m$—$OR^a$, $C_{1-3}$haloalkyloxy, —$SR^a$, —$N(R^c)_2$, —$CF_3$, —CN, —OCN, —SCN, —NO, —$NO_2$, —$N_3$, —$S(O)R^a$, —$S(O)_2R^a$, —$S(O)_2N(R^c)_2$, —$C(O)R^a$, —$C(O)N(R^c)_2$ or —$OC(O)R^a$;
each $R^{2a}$ is independently optionally substituted $C_{1-6}$alkyl, halo, —$OC_{1-6}$alkyl, —OH, —$N(C_{1-6}$alkyl$)_2$, —$N(H)C_{1-6}$alkyl, —CN, —$NO_2$, —$C(O)C_{1-6}$alkyl, —$CO_2H$, —$CO_2C_{1-6}$alkyl, —$C(O)N(H)C_{1-6}$alkyl or —$C(O)N(C_{1-6}$alkyl$)_2$;
each of $R^3$ and $R^4$ are, independently, —H, halo, optionally substituted $C_{1-6}$alkyl, optionally substituted $C_{3-8}$cycloalkyl, optionally substituted $C_{4-11}$cycloalkylalkyl, optionally substituted $C_{6-10}$aryl, optionally substituted $C_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl;
each $R^a$ is independently H, $C_{1-6}$alkyl, $C_{3-8}$cycloalkyl, $C_{4-11}$cycloalkylalkyl, $C_{6-10}$aryl, $C_{7-16}$arylalkyl, 3-10 membered heteroalicyclyl, 4-11 membered heteroalicyclylalkyl, 5-15 membered heteroaryl or 6-16 membered heteroarylalkyl;

each $R^c$ is independently $R^a$, or, alternatively, two $R^c$ are taken together with the nitrogen atom to which they are bonded to form a 3 to 10-membered heteroalicyclyl or a 5-10 membered heteroaryl which may optionally include one or more of the same or different additional heteroatoms and which is optionally substituted with one or more of the same or different $R^a$ and/or $R^d$ groups;
each $R^d$ is =O, —$OR^a$, —$OCF_3$, —$SR^a$, =$NR^a$, =$NOR^a$, —$N(R^a)_2$, halo, —$CF_3$, —CN, —NO, —$NO_2$, =$N_2$, —$N_3$, —$S(O)R^a$, —$S(O_2)R^a$, —$SO_3R^a$, —$S(O)N(R^a)_2$, —$S(O)_2N(R^a)_2$, —$OSO_3R^a$, —$C(O)R^a$, —$CO_2R^a$, —$C(O)N(R^a)_2$, —$(CH_2)_n$—$OR^a$, —$N(H)$—$S(O)_2R^a$, —$C(O)$—$C_{1-6}$haloalkyl, —$S(O)_2C_{1-6}$haloalkyl, —$OC(O)R^a$, —$O(CH_2)_n$—$OR^a$, —$S(CH_2)_n$—$OR^a$, —$NHC_{1-6}$ haloalkyl, —$N(R^a)$—$(CH_2)_n$—$OR^a$, —[N(H)C(O)]_n OR^a$ or —$N(R^a)C(O)C_{1-6}$haloalkyl.
optionally two $R^d$, taken together with the atom or atoms to which they are attached, combine to form a 3-10 membered partially or fully saturated mono or bicyclic ring, optionally containing one or more heteroatoms and optionally substituted with one or more $R^a$;
w is 0, 1, 2, 3 or 4;
each m is 1, 2 or 3; and
each n is 0, 1, 2 or 3.

In one embodiment, A is indolyl or isoindolinyl. In one embodiment, the A indolyl or isoindolyl is attached at the 5-yl or 6-yl of the parent indolyl ring. In one embodiment, the A indolyl or isoindolyl is also attached at its own 5-yl or 6-yl to the 5-yl or 6-yl of the parent indolyl ring. In one embodiment, $R^3$ and $R^4$ are H.

One embodiment is a compound according to formula V, and more specifically having formula Va:

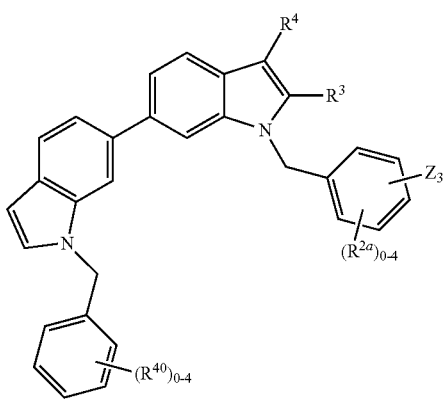

Va where each $R^{40}$ is independently $C_{1-6}$alkyl, halo, —$OC_{1-6}$alkyl, —OH, —$N(R^{80a})_2$, perhaloalkyl, —CN, —$NO_2$, —$CO_2C_{1-6}$alkyl or —$C(O)NR^{80a}R^{80a}$, where each $R^{80a}$ is independently H or $C_{1-6}$alkyl; and the remaining variables are as defined for formula V. In one embodiment, at least one of $R^{40}$ is —$OC_{1-6}$alkyl. In one embodiment, at least one $R^{40}$ is —$OC_{1-6}$alkyl para to the corresponding benzyl methylene. In one embodiment, at least one $R^{40}$ is —$OCH_3$ or —$OCH_2CH_3$, para to the corresponding benzyl methylene. In one embodiment, $R^3$ and $R^4$ are H.

One embodiment is a compound according to formula V, and more specifically having formula Vb:

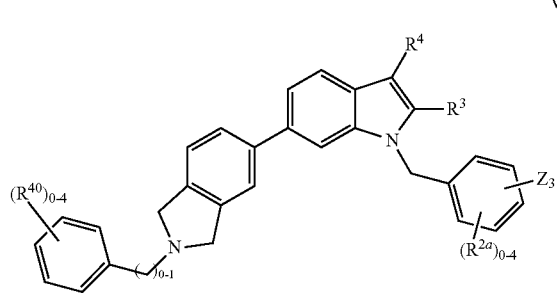

where each $R^{40}$ is independently $C_{1-6}$alkyl, halo, —$OC_{1-6}$alkyl, —OH, —$N(R^{80a})_2$, perhaloalkyl, —CN, —$NO_2$, —$CO_2C_{1-6}$alkyl or —$C(O)NR^{80a}R^{80a}$, where each $R^{80a}$ is independently H or $C_{1-6}$alkyl; and the remaining variables are as defined for formula V. In one embodiment, at least one of $R^{40}$ is —$OC_{1-6}$alkyl. In one embodiment, at least one $R^{40}$ is —$OC_{1-6}$alkyl para to the corresponding benzyl methylene or isoindolinyl nitrogen. In one embodiment, at least one $R^{40}$ is —$OCH_3$ or —$OCH_2CH_3$, para to the corresponding benzyl methylene or isoindolinyl nitrogen. In one embodiment, $R^3$ and $R^4$ are H.

One embodiment is a compound according to formula V, and more specifically having formula Vc:

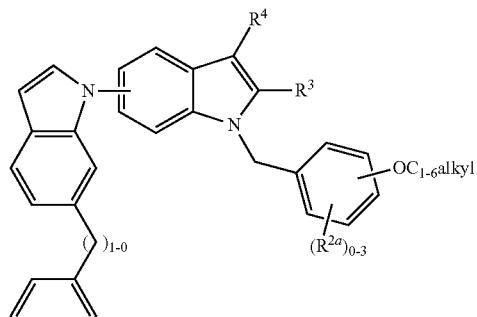

where each $R^{40}$ is independently $C_{1-6}$alkyl, halo, —$OC_{1-6}$alkyl, —OH, —$N(R^{80a})_2$, perhaloalkyl, —CN, —$NO_2$, —$CO_2C_{1-6}$alkyl, —$CO_2H$ or —$C(O)NR^{80a}R^{80a}$, where each $R^{80a}$ is independently H or $C_{1-6}$alkyl; and the remaining variables are as defined for formula V. In one embodiment, at least one of $R^{40}$ is —$CO_2H$. In one embodiment, the —$OC_{1-6}$alkyl on the ring bearing $R^{2a}$ is para to the corresponding benzyl methylene. In one embodiment, the —$OC_{1-6}$alkyl on the ring bearing $R^{2a}$ is —$OCH_3$ or —$OCH_2CH_3$ and is para to the corresponding benzyl methylene. In any of the aforementioned embodiments, the indol-1-yl group (ring A) is attached to the parent indolyl at the 5- or 6-yl position. In one embodiment, $R^3$ and $R^4$ are H.

Another embodiment is a compound or pharmaceutically acceptable salt thereof, from Table 1 or from Table 2. The compounds in Table 1 and Table 2 were prepared as described in the Experimental section below, but could also be prepared in other ways, as would be understood by one of ordinary skill in the art. In Tables 1 and 2, L is described as a group whose position is with respect to the parent indole ring. In Table 1, the groups Z and $R^1$ are described as a group whose position is relative to L; L being at position 1 of the phenyl ring to which it is attached. In Table 2, the groups Z and $R^1$ are described as a group whose position is with respect to the ring A on which they reside; ring A's position is described as where L attaches to ring A.

TABLE 1

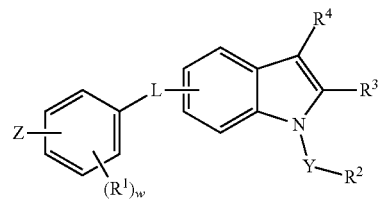

| Cpd | L | Y | Z | w | $R^1$ | $R^2$ | $R^3$ | $R^4$ |
|---|---|---|---|---|---|---|---|---|
| I-1 | $CH_2$-6-yl | — | 3-$CO_2H$ | 0 | — | H | H | H |
| I-2 | $CH_2$-6-yl | $CH_2$ | 3-$CO_2H$ | 0 | — | 4-methoxyphenyl | H | H |
| I-3 | $CH_2$-6-yl | — | 3-$CO_2H$ | 0 | — | H | H | $C(O)CO_2H$ |
| I-4 | $CH_2$-6-yl | $CH_2$ | 3-$CO_2H$ | 0 | — | 3-$CO_2H$-phenyl | H | H |
| I-5 | $CH_2$-6-yl | $CH_2$ | 3-$CO_2H$ | 0 | — | ![structure: HOOC-phenyl-CH2-indolyl] | H | H |
| I-6 | $CH_2$-6-yl | — | 3-$CO_2H$ | 0 | — | 3-$CO_2H$-phenyl | H | H |

TABLE 1-continued

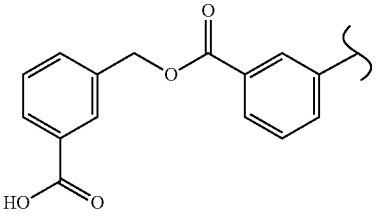 [SMILES: Cc1cccc(C(=O)OCc2cccc(C(=O)O)c2)c1]

| Cpd | L | Y | Z | w | R¹ | R² | R³ | R⁴ |
|---|---|---|---|---|---|---|---|---|
| I-7 | $CH_2$-6-yl | — | 3-$CO_2H$ | 0 | — | 3-methoxyphenyl | H | H |
| I-8 | $CH_2$-6-yl | — | 3-$CO_2H$ | 0 | — | H | H | C(O)H |
| I-9 | $CH_2$-5-yl | — | 3-$CO_2H$ | 0 | — | H | H | H |
| I-10 | $CH_2$-5-yl | $CH_2$ | 3-$CO_2H$ | 0 | — | 3-$CO_2H$-phenyl | H | H |
| I-11 | 6-yl | $CH_2$ | — | 1 | 3-$OCH_3$ | 3-$CO_2H$-phenyl | H | H |
| I-12 | 6-yl | — | 3-$CO_2H$ | 0 | — | H | H | H |
| I-13 | 5-yl | $CH_2$ | 3-$CO_2H$ | 0 | — | 3-$CO_2H$-phenyl | H | H |
| I-14 | 6-yl | $CH_2$ | — | 1 | 3-OH | 3-$CO_2H$-phenyl | H | H |
| I-15 | $CH_2$-6-yl | — | — | 1 | 3-$NO_2$ | H | H | H |
| I-16 | $CH_2$-6-yl | — | 3-$CO_2H$ | 1 | 6-$NO_2$ | H | H | H |
| I-17 | $CH_2$-6-yl | — | 3-$CO_2H$ | 1 | 6-$OCH_3$ | H | H | H |
| I-18 | $CH_2$-6-yl | — | 3-$CO_2H$ | 1 | 5-OH | H | H | H |
| I-19 | $CH_2$-6-yl | — | 3-$CO_2H$ | 1 | 6-OH | H | H | H |
| I-20 | $CH_2$-6-yl | — | 3-$CO_2H$ | 1 | 5-$OCH_3$ | H | H | H |
| I-21 | 6-yl | $CH_2$ | — | 1 | 3-(3-$CO_2H$-benzyloxy) | 3-$CO_2H$-phenyl | H | H |
| I-22 | 6-yl | $CH_2$ | — | 1 | 3-(4-methoxy-benzyloxy) | 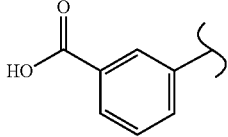 | H | H |

TABLE 2

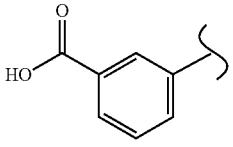

| Cpd | A | L | Y | Z | w | R¹ | R² | R³ | R⁴ |
|---|---|---|---|---|---|---|---|---|---|
| II-1 | quinolin-2-yl | 6-yl | $CH_2$ | — | 1 | 6-Cl | 3-$CO_2H$-phenyl (meta-carboxyphenyl) | H | H |
| II-2 | quinolin-2-yl | 5-yl | $CH_2$ | — | 1 | 6-Cl | 3-$CO_2H$-phenyl (meta-carboxyphenyl) | H | H |

TABLE 2-continued

| Cpd | A | L | Y | Z | w | R¹ | R² | R³ | R⁴ |
|---|---|---|---|---|---|---|---|---|---|
| II-3 | indol-6-yl | 6-yl | $CH_2$ | — | 1 | N-4-methoxybenzyl | 3-carboxybenzoyl (HOOC-C₆H₄-C(O)-) | H | H |

One embodiment is a compound, or pharmaceutically acceptable salt thereof, which is 3-((1H-indol-6-yl)methyl) benzoic acid (I-1); 3-((1-(4-methoxybenzyl)-1H-indol-6-yl) methyl)benzoic acid (I-2); 3-((3-(carboxycarbonyl)-1H-indol-6-yl)methyl)benzoic acid (I-3); 3-((1-(3-(carboxy)benzyl)-1H-indol-6-yl)methyl)benzoic acid (I-4); 3,3'-(1,1'-methylenebis(1H-indole-6,1-diyl))bis(methylene)dibenzoic acid (I-5); 3-(6-(3-carboxybenzyl)-1H-indol-1-yl)benzoic acid (I-6); 3-((1-(3-methoxyphenyl)-1H-indol-6-yl)methyl) benzoic acid (I-7); 3-((3-formyl-1H-indol-6-yl)methyl)benzoic acid (I-8); 3-((1H-indol-5-yl)methyl)benzoic acid (I-9); 3-((1-(3-carboxybenzyl)-1H-indol-5-yl)methyl)benzoic acid (I-10); 3-((6-(3-methoxyphenyl)-1H-indol-1-yl)methyl)benzoic acid (I-11); 3-(1H-indol-6-yl)benzoic acid (I-12); 3-(1-(3-carboxybenzyl)-1H-indol-5-yl)benzoic acid (I-13); 3-((6-(3-hydroxyphenyl)-1H-indol-1-yl)methyl)benzoic acid (I-14); 6-(3-nitrobenzyl)-1H-indole (I-15); 3-((1H-indol-6-yl)methyl)-4-nitrobenzoic acid (I-16); 3-((1H-indol-6-yl) methyl)-4-methoxybenzoic acid (I-17); 3-((1H-indol-6-yl) methyl)-5-hydroxybenzoic acid (I-18); 3-((1H-indol-6-yl) methyl)-4-hydroxybenzoic acid (I-19); 3-((1H-indol-6-yl) methyl)-5-methoxybenzoic acid (I-20); 3-((3-(1-(3-carboxybenzyl)-1H-indol-6-yl)phenoxy)methyl)benzoic acid (I-21); 3-((3-((6-(3-(4-methoxybenzyloxy)phenyl)-1H-indol-1-yl)methyl)benzoyloxy)methyl)benzoic acid (I-22); 3-((6-(6-chloroquinolin-2-yl)-1H-indol-1-yl)methyl)benzoic acid (II-1); 3-((5-(6-chloroquinolin-2-yl)-1H-indol-1-yl)methyl)benzoic acid (II-2) or 3-((1'-(4-methoxybenzyl)-1H,1'H-6,6'-biindol-1-yl)methyl)benzoic acid (II-3).

Pharmaceutical Compositions

As mentioned, another embodiment is a pharmaceutical composition including a compound as described in any of the embodiments above. Another embodiment is a unit dosage formulation including the described pharmaceutical composition. Pharmaceutical compositions described herein can be manufactured by means of conventional mixing, dissolving, granulating, dragee-making levigating, emulsifying, encapsulating, entrapping, or lyophilization processes. The compositions can be formulated in conventional manner using one or more physiologically acceptable carriers, diluents, excipients, or auxiliaries which facilitate processing of the active compounds into preparations which can be used pharmaceutically.

Compounds can be provided in a variety of formulations and dosages. The compounds can be provided in a pharmaceutically acceptable form, including where the compound can be formulated in the pharmaceutical compositions per se, or in the form of a hydrate, solvate, N-oxide, or pharmaceutically acceptable salt, as described herein. Typically, such salts are more soluble in aqueous solutions than the corresponding free acids and bases, but salts having lower solubility than the corresponding free acids and bases can also be formed. It is to be understood that reference to the compound or "active" in discussions of formulations is also intended to include, where appropriate as known to those of skill in the art, formulation of the prodrugs of the compounds.

In one embodiment, the compounds are provided as non-toxic pharmaceutically acceptable salts, as noted previously. Suitable pharmaceutically acceptable salts of the compounds described herein include acid addition salts such as those formed with hydrochloric acid, fumaric acid, p-toluenesulphonic acid, maleic acid, succinic acid, acetic acid, citric acid, tartaric acid, carbonic acid, or phosphoric acid. Salts of amine groups can also include quaternary ammonium salts in which the amino nitrogen atom carries a suitable organic group such as an alkyl, alkenyl, alkynyl, or substituted alkyl moiety. Furthermore, where the compounds carry an acidic moiety, suitable pharmaceutically acceptable salts thereof can include metal salts such as alkali metal salts, e.g., sodium or potassium salts; and alkaline earth metal salts, e.g., calcium or magnesium salts.

The pharmaceutical compositions for the administration of the compounds can be conveniently presented in dosage unit form and can be prepared by any of the methods well known in the art of pharmacy. The pharmaceutical compositions can be, for example, prepared by uniformly and intimately bringing the active ingredient into association with a liquid carrier, a finely divided solid carrier or both, and then, if necessary, shaping the product into the desired formulation. In the pharmaceutical composition the active object compound is included in an amount sufficient to produce the desired therapeutic effect.

One embodiment is the pharmaceutical compositions of the invention, or the unit dosage formulation thereof, suitable for administration orally, intravenously, intra-arterially, intrathecally, intradermally, intracavitarily, rectally, intramuscularly, subcutaneously, intracisternally, intravaginally, intraperitonially, topically, buccally and nasally.

The compounds can be administered by oral, parenteral (e.g., intramuscular, intraperitoneal, intravenous, ICV, intracisternal injection or infusion, subcutaneous injection, or implant), by inhalation spray nasal, vaginal, rectal, sublingual, urethral (e.g., urethral suppository) or topical routes of administration (e.g., gel, ointment, cream, aerosol, etc.) and can be formulated, alone or together, in suitable dosage unit formulations containing conventional non-toxic pharmaceutically acceptable carriers, adjuvants, excipients, and vehicles appropriate for each route of administration.

Administration of the compounds described herein, or their pharmaceutically acceptable salts, in pure form or in an appropriate pharmaceutical composition, can be carried out via any of the accepted modes of administration or agents for serving similar utilities. Thus, administration can be, for example, orally, nasally, parenterally (intravenous, intramuscular, or subcutaneous), topically, transdermally, intravaginally, intravesically, intracisternally, or rectally, in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages.

For topical administration, the HIV-1 fusion compound(s) or prodrug(s) can be formulated as solutions, gels, ointments, creams, suspensions, etc., as are well-known in the art. Such formulations can be included in a patch or other transdermal delivery system or formulation, e.g., a formulation with ingredients specifically designed to aid transport of the compound through the skin and into the body tissues.

Systemic formulations include those designed for administration by injection (e.g., subcutaneous, intravenous, intramuscular, intrathecal, or intraperitoneal injection) as well as those designed for transdermal, transmucosal, oral, or pulmonary administration.

Useful injectable preparations include sterile suspensions, solutions, or emulsions of the active compound(s) in aqueous or oily vehicles. The compositions can also contain formulating agents, such as suspending, stabilizing, and/or dispersing agents. The formulations for injection can be presented in unit dosage form, e.g., in ampules or in multidose containers, and can contain added preservatives.

Alternatively, the injectable formulation can be provided in powder form for reconstitution with a suitable vehicle, including but not limited to sterile pyrogen free water, buffer, and dextrose solution, before use. To this end, the active compound(s) can be dried by any art-known technique, such as lyophilization, and reconstituted prior to use. The pharmaceutical compositions can be in the form of a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent. Among the acceptable vehicles and solvents that can be employed are water, Ringer's solution, and isotonic sodium chloride solution.

For transmucosal administration, penetrants appropriate to the barrier to be permeated are used in the formulation. Such penetrants are known in the art.

For oral administration, the pharmaceutical compositions can take the form of, for example, lozenges, tablets, or capsules prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulfate). The tablets can be coated by methods well known in the art with, for example, sugars, films, or enteric coatings. Additionally, the pharmaceutical compositions containing the 2,4-substituted pyridinediamine as active ingredient or prodrug thereof in a form suitable for oral use can also include, for example, tHoffman LaRoches, lozenges, aqueous, or oily suspensions, dispersible powders or granules, emulsions, hard or soft capsules, or syrups or elixirs. Compositions intended for oral use can be prepared according to any method known to the art for the manufacture of pharmaceutical compositions, and such compositions can contain one or more agents including sweetening agents, flavoring agents, coloring agents, and preserving agents in order to provide pharmaceutically elegant and palatable preparations. Tablets contain the active ingredient (including drug and/or prodrug) in admixture with non-toxic pharmaceutically acceptable excipients which are suitable for the manufacture of tablets. These excipients can be for example, inert diluents, such as calcium carbonate, sodium carbonate, lactose, calcium phosphate or sodium phosphate; granulating and disintegrating agents (e.g., corn starch or alginic acid); binding agents (e.g. starch, gelatin, or acacia); and lubricating agents (e.g., magnesium stearate, stearic acid, or talc). The tablets can be left uncoated or they can be coated by known techniques to delay disintegration and absorption in the gastrointestinal tract and thereby provide a sustained action over a longer period. For example, a time delay material such as glyceryl monostearate or glyceryl distearate can be employed. They can also be coated by the techniques described in the U.S. Pat. Nos. 4,256,108; 4,166,452; and 4,265,874 to form osmotic therapeutic tablets for control release. The pharmaceutical compositions described herein can also be in the form of oil-in-water emulsions. Preparations for oral administration can be suitably formulated to give controlled release of the active compound, as is well known.

Liquid preparations for oral administration can take the form of, for example, elixirs, solutions, syrups, or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives, or hydrogenated edible fats); emulsifying agents (e.g., lecithin, or acacia); non-aqueous vehicles (e.g., almond oil, oily esters, ethyl alcohol, Cremophore™, or fractionated vegetable oils); and preservatives (e.g., methyl or propyl-p-hydroxybenzoates or sorbic acid). The preparations can also contain buffer salts, preservatives, flavoring, coloring, and sweetening agents as appropriate.

For buccal administration, the compositions can take the form of tablets or lozenges formulated in the conventional manner.

For rectal and vaginal routes of administration, the active compound(s) can be formulated as solutions (for retention enemas), suppositories, or ointments containing conventional suppository bases such as cocoa butter or other glycerides. In particular embodiments, the compounds can be formulated as urethral suppositories For nasal administration or administration by inhalation or insufflation, the active compound(s) or prodrug(s) can be conveniently delivered in the form of an aerosol spray from pressurized packs or a nebulizer with the use of a suitable propellant (e.g., dichlorodifluoro-methane, trichlorofluoromethane, dichlorotetrafluoroethane, fluorocarbons, carbon dioxide, or other suitable gas). In the case of a pressurized aerosol, the dosage unit can be determined by providing a valve to deliver a metered amount. Capsules and cartridges for use in an inhaler or insufflator (for example, capsules and cartridges including gelatin) can be formulated containing a powder mix of the compound and a suitable powder base such as lactose or starch.

Another embodiment is a compound or pharmaceutical composition disclosed herein for use in inhibiting HIV-1 cell fusion.

Another embodiment is a compound or pharmaceutical composition disclosed herein for use in inhibiting HIV-1 infectivity.

Another embodiment is a compound or pharmaceutical composition disclosed herein for use in treating a symptom or effect of HIV-1 infection in a subject.

Methods

The present invention provides compounds and pharmaceutical compositions thereof, as described herein, for use in therapy for the conditions in which targeting of the HIV-1 fusion pathway is therapeutically useful. The present invention further provides use of the compounds of the present invention in the manufacture of a medicament for the treatment of such conditions The methods can be practiced as a therapeutic approach towards the treatment of the conditions described herein. Thus, in a specific embodiment, the compounds (and the various forms described herein, including pharmaceutical formulations including the compounds (in the various forms)) can be used to treat the conditions described herein in animal subjects, including humans. The methods generally include administering to the subject an amount of a compound described herein, or a salt, prodrug, hydrate, or N-oxide thereof, effective to treat the condition. In one embodiment, the subject is a non-human mammal, including, but not limited to, a primate. In another embodiment, the subject is a human.

As noted previously, "treating" or "treatment" of a disease in a patient refers to (1) preventing the disease from occurring in a patient that is predisposed (e.g., has experienced an exposure to HIV-1) or does not yet display symptoms of the disease; (2) inhibiting the disease or arresting its development; or (3) ameliorating or causing regression of the disease. As well understood in the art, "treatment" is an approach for obtaining beneficial or desired results, including clinical results. For the purposes of this invention, beneficial or desired results can include one or more, but are not limited to, alleviation or amelioration of one or more symptoms, diminishment of extent of a condition, including a disease, stabilized (i.e., not worsening) state of a condition, including diseases, preventing spread of disease, delay or slowing of condition, including disease, progression, amelioration or palliation of the condition, including disease state, and remission (whether partial or total), whether detectable or undetectable. Preferred are compounds that are relatively potent compared to the class as a whole and can be administered at low doses.

Dosage amounts will typically be in the range of from about 0.0001 or 0.001 or 0.01 mg/kg/day to about 100 mg/kg/day, but can be higher or lower, depending upon, among other factors, the activity of the compound, its bioavailability, the mode of administration, and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day, or multiple times per day, depending upon, among other things, the mode of administration, the specific indication being treated, and the judgment of the prescribing physician. In cases of local administration or selective uptake, such as local topical administration, the effective local concentration of active compound(s) may not be related to plasma concentration. Skilled artisans will be able to optimize effective local dosages without undue experimentation.

The compounds described herein are inhibitors of HIV-1 fusion and as a consequence of this activity, the compounds can be used in a variety of in vitro, in vivo, and ex vivo contexts to regulate or inhibit HIV-1 fusion. One embodiment is a method described herein, directed to use of a single compound species described herein.

One embodiment is a method of inhibiting HIV-1 cell fusion, the method including contacting cells with an effective amount of a compound or pharmaceutical composition disclosed herein.

Another embodiment is a method of inhibiting HIV-1 infectivity, the method including contacting cells with an effective amount of a compound or pharmaceutical composition disclosed herein.

Another embodiment is a method of treating a symptom or effect of HIV-1 infection in a subject, the method including administering to the subject an effective amount of a compound or pharmaceutical composition disclosed herein. A more specific embodiment includes co-administration of an agent that mitigates a symptom or effect of HIV-1 infection, where the agent is a nucleoside analog reverse transcriptase inhibitor, a protease inhibitor, an integrase inhibitor, a maturation inhibitor, a non nucleoside analog reverse transcriptase inhibitor, a cell fusion inhibitor or a nucleotide reverse transcriptase inhibitor. One or more such agents may be used in combination, so long as not specifically contraindicated. In a more specific embodiment the agent is abacavir, atazanavir, darunavir, delaviridine, didanosine, efavirenz, enfuvirtide, emtricitabine, etravirine, fosamprenavir, indinavir, lamivudine, lopinavir, maraviroc, nelfinavir, nevirapine, raltegravir, ritonavir, saquinovir, stavudine, tenofovir, tipranavir, zalcitabine or zidovudine. In another embodiment, the agent is abacavir (currently available under the brand name, Ziagen, available from GlaxoSmithKline), tipranavir (currently available under the brand name, Aptivus, available from Boehringer Ingelheim Pharmaceuticals), efavirenz, emtricitabine, and tenofovir (currently available in combination under the brand name, Atripla, available from Bristol-Myers Squibb & Gilead Sciences, LLC.), zidovudine (currently available under the brand name, AZT, available from GlaxoSmithKline), lamivudine and zidovudine (currently available under the brand name, Combivir, available from GlaxoSmithKline), indinavir (currently available under the brand name, Crixivan, available from Merck & Co.), delaviridine (currently available under the brand name, Rescriptor, available from Pfizer), efavirenz (currently available under the brand name, Sustiva, available from Bristol-Myers Squibb), emtricitabine (currently available under the brand name, Emtriva, available from Bristol-Myers Squibb), Lamivudine (currently available under the brand name, Epivir, available from GlaxoSmithKline), abacavir and lamivudine (currently available under the brand name, Epzicom, available from GlaxoSmithKline), saquinovir (currently available under the brand name, Fortovase, available from Hoffman LaRoche), enfuvirtide (currently available under the brand name, Fuzeon, available from Hoffman LaRoche), zalcitabine (currently available under the brand name, Hivid, available from Hoffman LaRoche), etravirine (currently available under the brand name, Intelence, available from Tibotec), raltegravir (currently available under the brand name, Isentress, available from Merck & Co.), lopinavir (currently available under the brand name, Kaletra, available from Abbott), fosamprenavir (currently available under the brand name, Lexiva, available from GlaxoSmithKline), Nevirapine (currently available under the brand name, Viramune, available from Boehringer Ingelheim Pharmaceuticals), ritonavir (currently available under the brand name, Norvir, available from Abbot), darunavir (currently available under the brand name, Prezista, available from Tibotec), atazanavir (currently available under the brand name, Reyataz, available from Bristol-Meyers Squibb), maraviroc (currently available under the brand name, Selzentry, available from Pfizer), stavudine (currently available under the brand name, Zerit, available from Bristol-Meyers Squibb), abacavir, lamivudine and zidovudine (currently available under the brand name, Trizivir, available from GlaxoSmithKline), tenofovir and emtricitabine (currently available under the brand name, Truvada, available from Gilead Sciences, LLC.), didanosine (currently available under the brand name, Videx, available from Bristol-Meyers Squibb), nelfinavir (currently available under the brand name, Viracept, available from Hoffman-LaRoche) or tenofovir disoproxil fumarate (currently available under the brand name, Viread, available from Gilead Sciences, LLC.).

Another embodiment is use of a compound or pharmaceutical composition disclosed herein in the manufacture of a medicament for inhibiting HIV-1 cell fusion.

Another embodiment is use of a compound or pharmaceutical composition disclosed herein to inhibit HIV-1 infectivity.

Another embodiment is use of a compound or pharmaceutical composition disclosed herein to treat a symptom or effect of HIV-1 infection in a subject.

Another embodiment is a compound or pharmaceutical composition as described herein for use in inhibiting HIV-1 cell fusion or for use in inhibiting HIV-1 infectivity or for use in treating a symptom or effect of HIV-1 infection in a subject.

Another embodiment is use of a compound or pharmaceutical composition as described herein in the manufacture of a medicament for inhibiting HIV-1 cell fusion or to inhibit HIV-1 infectivity or to treat a symptom or effect of HIV-1 infection in a subject.

Specific examples of assays and experimental details relating to the methods are described below.

EXPERIMENTAL

Compound Synthesis

In general, compounds were synthesized using standard coupling reactions with appropriately functionalized aryl partners to make the scaffold of compounds of the invention, followed by in some cases appropriate additional functionalization as required. For example, compounds according to Formula I, where, for example, L is —$CH_2$—, A is phenyl and $X^1$ and $X^2$ are carbon, can be prepared via a Suzuki reaction of an aryl boronic acid and a substituted halomethylindole, for example an indole-$CH_2Br$, or, for example, a halomethylaryl and an indole boronic acid, as shown in Scheme 1. Compounds of Formula I where L is longer than one carbon, for example two or three carbons, can be prepared in an analogous manner by coupling two aromatic partners via, e.g. Wittig homologation, reduction of the alkene formed therefrom, and like reactions well known to skilled artisans.

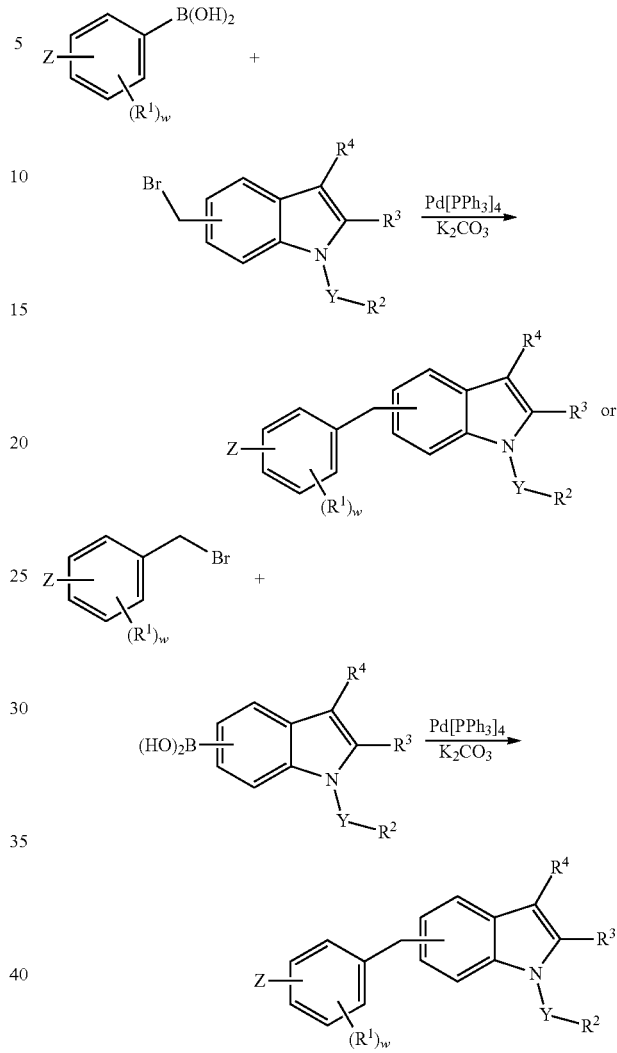

In another example, compounds according to Formula I where, for example, L is a bond, A is phenyl and $X^1$ and $X^2$ are carbon, can be prepared via Suzuki reaction of an indole boronic acid and a substituted aryl halide (or aryl boronic acid and indole halide), for example an appropriately functionalized phenyl iodide as shown in Scheme 2.

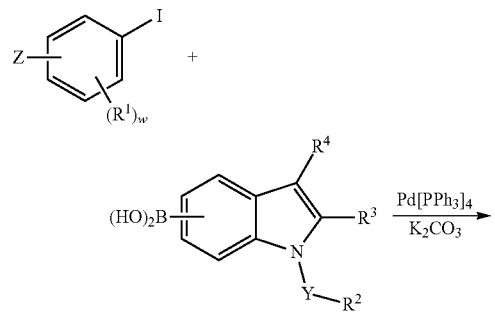

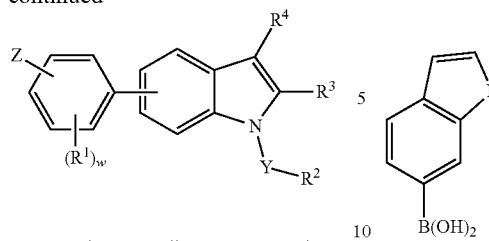

In another example, compounds according to Formula I where, for example, L is —O—, A is phenyl and $X^1$ and $X^2$ are carbon, can be prepared via, e.g., Ullmann Ether Synthesis of an appropriately substituted hydroxyindole and a substituted aryl halide, for example an appropriately functionalized phenyl bromide as shown in Scheme 3. Bisarylthioethers, compounds of Formula I where L is —S—, can also be prepared in this manner.

Scheme 3

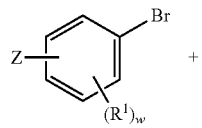

+

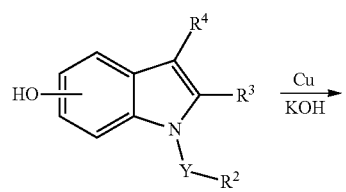

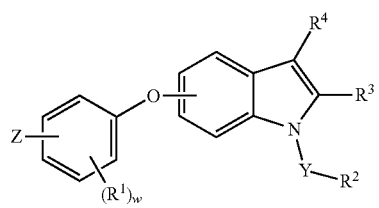

Further substitutions at the indole ring can be achieved, for example, by nucleophilic attack on the indole nitrogen to provide —Y—$R^2$ substitution or by Ullman reaction. Substitutions for $R^3$ and $R^4$ are well known indole chemistry as would be understood by one of ordinary skill in the art.

Functionalization of corresponding benzimidazoles, azaindoles, indolines and isoindolines is well known in the art, and thus, these corresponding analogs are within the scope of the invention. For example, Scheme 4 depicts a method of substituting at, for example, C6 of an indole ring as represented in various specific examples below (where $R^{2a}$ is as described herein). C5 analogs were made using the corresponding 5-yl boronic acids. One of ordinary skill in the art would appreciate that 5-yl methylenehalides and the corresponding aryl boronic acids could also be used to make the identical products. The choice of which reaction partner is the boronic acid and which is the halide may depend on, for example, commercial availability or ease of synthesis of one or both of the reaction partners.

Scheme 4

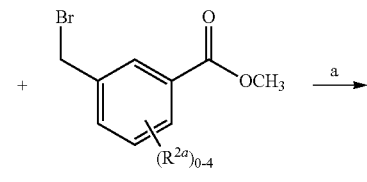

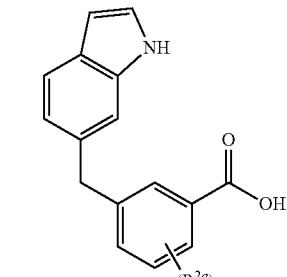

a) Pd[PPh$_3$]$_4$, K$_2$CO$_3$, THF, N$_2$, 80° C.; b) MeOH/NaOH, 2M HCl;

In another example, Scheme 5 depicts a method of substituting N1 of an indole ring as represented in various specific examples below (where $R^{2a}$ is as described herein). One of ordinary skill in the art would appreciate that N-aryl indoles are made, for example, via nucleophilic aromatic substitution reactions with haloaryl tricarbonylchromium complexes or other organometallic coupling reactions.

Although many of the synthetic schemes discussed do not illustrate the use of protecting groups, skilled artisans will recognize that in some instances certain substituents, such as, for example, Z, $R^2$ and/or other groups, can include functionality requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in *Protective Groups in Organic Synthesis*, Greene & Wuts, $2^{nd}$ Ed., John Wiley & Sons, New York, 1991 (especially pages 10-142 (alcohols, 277-308 (thiols) and 309-405 (amines) the disclosure of which is incorporated herein by reference for its description of protecting groups and their use).

Scheme 5

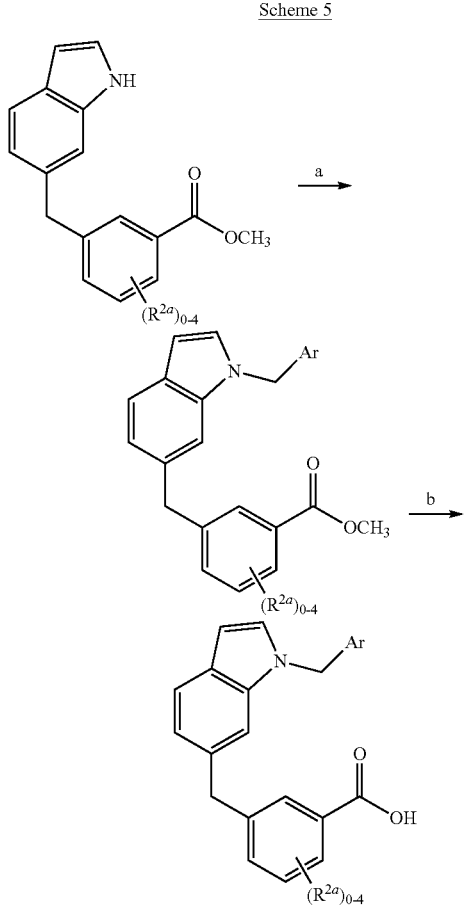

a) NaH/DMF; Methyl-3-(bromomethyl)benzoate b) MeOH/NaOH, 2M HCl

EXAMPLES

The invention is further understood by reference to the following examples, which are not intended to be limiting. Any synthetic methods that are functionally equivalent are within the scope of the invention. Various modifications of the embodiments described herein would be apparent to one of ordinary skill in the art from the foregoing description. Such modifications fall within the scope of the appended claims. Compound synthesis was confirmed by LC-MS and proton NMR.

Synthesis of 3-((1H-indol-6-yl)methyl)benzoic acid, compound I-1: Indole-6-boronic acid, 386 mg (2.4 mmol) and methyl-3-(bromomethyl)benzoate, 460 mg (2.0 mmol), were added into a 100 ml round-bottomed flask containing 15 ml THF, and then 230 mg of $Pd(PPh_3)_4$ was added, followed by 3 ml of 2M aqueous $K_2CO_3$. The mixture was stirred and heated to 80° C. under $N_2$ for over 4 hours. The reaction was monitored by TLC. After the reaction was complete, the mixture was cooled to room temperature, 10 ml $H_2O$ was added and the product extracted with ethyl acetate (10 ml×3). The organic solvent was combined and dried with anhydrous $Na_2SO_4$, filtered and evaporated to dryness. The crude product was purified by chromatographic column using hexane: ethyl acetate (7:1) as eluent. The ester, 360 mg, was obtained as a pale yellow solid, yield 67%. A portion of the ester, 20 mg, was dissolved in 4 ml THF:methanol (4:1), and 1 ml 25% aqueous NaOH was added. The mixture was stirred for 3 hours at room temperature, then adjusted to pH 3.0 using 2M HCl. The solution was extracted with $CH_2Cl_2$, 3×15 ml. The organic solvent was combined and dried with $Na_2SO_4$, then evaporated to dryness. The final product was purified by HPLC using acetonitrile/$H_2O$ as eluent. The acetonitrile was removed from the eluent, the eluent frozen and lyophilized. After lyophilization, 11 mg target compound was obtained as a grey powder.

Analysis: Mass calculated for $C_{16}H_{13}NO_2$: 251; LCMS: 252.6 $(M+H)^+$; $^1H$ NMR (400 MHz, DMSO-$d_6$) δ ppm 7.80 (1H, s), 7.75 (1H, d, J=7.3 Hz), 7.51 (1H, d, J=7.9 Hz), 7.41 (2H, m), 7.26 (1H, t, J=3.0 Hz), 7.21 (1H, s), 6.87 (1H, dd, J=7.9 Hz, J=1.2 Hz), 6.35 (1H, s), 4.08 (2H, s).

Other compounds synthesized using this or a similar method are:

3-((1H-indol-6-yl)methyl)-4-nitrobenzoic acid (I-16) Mass calculated for $C_{16}H_{12}N_2O_4$: 296; LCMS: 297.8 (M+H)'; $^1HNMR$ (400 MHz, DMSO-$d_6$) δ ppm 7.98 (3H, m), 7.45 (1H, d, J=7.9 Hz), 7.29 (1H, t, J=3.0 Hz), 7.13 (1H, s), 6.80 (1H, dd, J=1.2 Hz, J=7.9 Hz), 6.36 (1H, s), 4.33 (2H, s).

3-((1H-indol-6-yl)methyl)-4-methoxybenzoic acid (I-17): Mass calculated for $C_{17}H_{15}NO_3$: 281; LCMS: 282.8 $(M+H)^+$; $^1HNMR$ (400 MHz, DMSO-$d_6$) δ ppm 7.80 (1H, m), 7.65 (1H, s), 7.41 (1H, m), 7.25 (1H, s), 7.16 (1H, s), 7.08 (1H, d, J=7.3 Hz), 6.87 (1H, m), 6.35 (1H, s), 4.00 (2H, s), 3.88 (3H, s).

3-((1H-indol-6-yl)methyl)-5-methoxybenzoic acid (I-20): Mass calculated for $C_{17}H_{15}NO_3$: 281; LCMS: 282.6 $(M+H)^+$; $^1HNMR$ (400 MHz, DMSO-$d_6$) δ ppm 7.44 (1H, d, J=8.5 Hz), 7.39 (1H, s), 7.26 (2H, m), 7.22 (1H, s), 7.09 (1H, t, J=1.8 Hz), 6.88 (1H, dd, J=8.5 Hz J=1.2 Hz), 6.35 (1H, s), 4.05 (2H, s), 3.77 (3H, s).

3-((1H-indol-6-yl)methyl)-5-hydroxybenzoic acid (I-18): Mass calculated for $C_{16}H_{13}NO_3$: 267; LCMS: 268.3 (M+H)'; $^1HNMR$ (400 MHz, DMSO-$d_6$) δ ppm 7.44 (1H, d, J=7.9 Hz), 7.26 (2H, m), 7.19 (1H, s), 7.13 (1H, d, J=1.8 Hz), 6.85 (2H, m), 6.35 (1H, t, J=1.8 Hz), 3.98 (2H, s).

3-((1H-indol-6-yl)methyl)-4-hydroxybenzoic acid (I-19): Mass calculated for $C_{16}H_{13}NO_3$: 267; LCMS: 268.3 $(M+H)^+$; $^1HNMR$ (400 MHz, DMSO-$d_6$) δ ppm 7.60 (2H, m), 7.42 (1H, d, J=7.9 Hz), 7.33 (1H, d, J=7.9 Hz), 7.14 (1H, d, J=1.2 Hz), 7.04 (1H, t, J=7.9 Hz), 6.90 (2H, m), 3.96 (2H, s).

Synthesis of 3-((3-(carboxycarbonyl)-1H-indol-6-yl)methyl)benzoic acid (I-3): 32 mg of methyl 3-(1H-indol-6-ylmethyl)benzoate was treated by 2M oxalyl dichloride in methylene chloride for 4 hours. Then following the general procedure above, 3.4 mg target compound was achieved as a yellow powder. Mass calculated for $C_{18}H_{13}NO_5$: 323; LCMS: 324.6 $(M+H)^+$; $^1HNMR$ (400 MHz, DMSO-$d_6$) δ ppm 8.37 (1H, d, J=3.0 Hz), 8.07 (1H, d, J=7.9 Hz), 7.81 (1H, s), 7.76 (1H, d, J=7.9 Hz), 7.52 (1H, d, J=7.9 Hz), 7.43 (1H, br), 7.37 (1H, s), 7.16 (1H, d, J=7.9 Hz), 4.13 (2H, s).

Synthesis of 3,3'-(1,1'-methylenebis(1H-indole-6,1-diyl)) bis(methylene)dibenzoic acid (I-5): 32 mg of methyl 3-(1H-indol-6-ylmethyl)benzoate was dissolved into 3 ml DMSO, then 56 mg KOH was added; the mixture was stirred at room temperature overnight under $N_2$ atmosphere. Then 50 µl $CH_2Cl_2$ was added, the mixture was stirred for 8 hours at room temperature. Then following the general procedures described herein, 3.6 mg target compound was purified to give an orange powder. Mass calculated for $C_{33}H_{26}N_2O_4$: 514; LCMS: 515.1 $(M+H)^+$ $^1H$ NMR (400 MHz, DMSO-$d_6$) δ ppm 7.84 (2H, s), 7.79 (2H, s), 7.74 (2H, d, J=7.7 Hz), 7.63 (2H, d, J=3.2 Hz), 7.48 (2H, d, J=7.7 Hz), 7.39 (2H, d, J=1.9 Hz), 7.37 (2H, d, J=1.9 Hz), 6.90 (2H, d, J=8.3 Hz), 6.57 (2H, s), 6.35 (2H, d, J=2.6 Hz), 4.07 (4H, s).

Synthesis of 3-((3-formyl-1H-indol-6-yl)methyl)benzoic acid: (I-8): 3 ml anhydrous DMF was cooled in ice-water bath, then 50 μl POCl$_3$ was added, the solution was stirred about 15 minutes, then 32 mg of methyl 3-(1H-indol-6-ylmethyl)benzoate in 2 ml DMF was added. The mixture was heated to 40° C. for 3 hours. After cooling to room temperature, the mixture was treated by cold water, following the general procedure above, the target compound was purified as a brown solid. Mass calculated for $C_{17}H_{13}NO_3$: 279; LCMS: 280.6 (M+H)$^+$; $^1$H NMR (400 MHz, DMSO-d$_6$) δ ppm 9.87 (1H, s), 8.24 (1H, d, J=3.0 Hz), 7.99 (1H, s), 7.80 (1H, d, J=7.3 Hz), 7.76 (1H, d, J=7.9 Hz), 7.52 (1H, d, J=7.9 Hz), 7.41 (1H, t, J=7.9 Hz), 7.34 (1H, s), 7.12 (1H, d, J=7.3 Hz), 4.12 (2H, s).

Synthesis of 3-((1-(4-methoxybenzyl)-1H-indol-6-yl)methyl)benzoic acid (I-2): 32 mg of methyl 3-(1H-indol-6-ylmethyl)benzoate was dissolved into 4 ml anhydrous DMF, and 15 mg sodium hydride in oil (60%). The mixture was protected by N$_2$ and stirred for 1 hour at room temperature. The mixture was cooled by ice-water bath and 25 mg 4-methoxybenzyl bromide was added. The mixture was stirred at room temperature overnight. TLC indicated no starting material remained; the reaction was stopped by adding 10 ml water. The solution was extracted with ethyl acetate (15 ml×3). The organic solvent was combined and dried with Na$_2$SO$_4$, then evaporated to dryness, directly used for next step without more purification. The ester group was saponified, for example, as described herein to yield the target compound; 5.0 mg target compound was obtained as an off-white powder. Mass calculated for $C_{24}H_{21}NO_3$: 371; LCMS: 371.9 (M+H)$^+$; $^1$H NMR (400 MHz, DMSO-d$_6$) δ ppm 7.77 (1H, s), 7.72 (1H, d, J=7.7 Hz), 7.49 (1H, d, J=7.0 Hz), 7.43 (1H, d, J=2.5 Hz), 7.34 (3H, br), 7.14 (2H, d, J=8.3 Hz), 6.95 (1H, d, J=7.7 Hz), 6.82 (2H, d, J=8.3 Hz), 6.37 (1H, d, J=2.6 Hz), 5.27 (2H, s), 4.04 (2H, s), 3.67 (3H, s).

Other compounds synthesized using this method include:

3-((1-(3-(carboxy)benzyl)-1H-indol-6-yl)methyl)benzoic acid (I-4): Mass calculated for $C_{24}H_{14}NO_4$: 385; LCMS: 386.5 (M+H)$^+$; $^1$H NMR (400 MHz, DMSO-d$_6$) δ ppm 7.77 (1H, s), 7.72 (2H, br), 7.68 (1H, m), 7.60 (1H, d, J=7.9 Hz), 7.45 (1H, d, J=3.0 Hz), 7.34 (3H, m), 7.29 (2H, br), 7.09 (1H, d, J=7.9 Hz), 6.57 (1H, s), 5.42 (2H, s), 4.09 (2H, s).

Synthesis of 3-((1H-indol-5-yl)methyl)benzoic acid (I-9): Indole-5-boronic acid, 193 mg (1.2 mmol) and methyl-3-(bromomethyl)benzoate, 230 mg (1.0 mmol) were added into a 100 ml round-bottomed flask containing 15 ml THF, then 50 mg Pd(PPh$_3$)$_4$ was added, followed by 2 ml 2M K$_2$CO$_3$. The mixture was stirred and heated to 80° C. under N$_2$ protection for over 4 hours. The reaction was monitored by TLC. After the reaction was completed and the mixture was cooled to room temperature, 10 ml H$_2$O was added and the product extracted with ethyl acetate (15 ml×3). The organic solvent was combined and dried with anhydrous Na$_2$SO$_4$, filtered and evaporated to dryness. The crude product was purified by chromatographic column using hexane:ethyl acetate (7:1) as eluent. 260 mg methyl 3-(1H-indol-5-ylmethyl)benzoate was obtained as a pale yellow solid, yield 48%. Saponification of the ester yielded the target compound, 8.2 mg target compound was obtained as a grey powder. Mass calculated for $C_{16}H_{13}NO_2$: 251; LCMS: 252.6 (M+H)$^+$; $^1$HNMR (400 MHz, DMSO-d$_6$) δ ppm 7.78 (1H, s), 7.74 (1H, d, J=7.9 Hz), 7.50 (1H, d, J=7.3 Hz), 7.38 (2H, m), 7.29 (2H, m), 6.95 (1H, dd, J=8.5 Hz, J=1.2 Hz), 6.35 (1H, s), 4.05 (2H, s).

Following the same or similar procedure the following compounds were made:

3-((1-(3-carboxybenzyl)-1H-indol-5-yl)methyl)benzoic acid (I-10): Mass calculated for $C_{24}H_{14}NO_4$: 385; LCMS: 386.7 (M+H)$^+$; $^1$H NMR (400 MHz, DMSO-d$_6$) δ ppm 7.78 (3H, d, J=7.9 Hz), 7.73 (1H, d, J=7.9 Hz), 7.49 (2H, br), 7.40 (4H, br), 7.35 (1H, d, J=8.5 Hz), 6.97 (1H, d, J=8.5 Hz), 6.43 (1H, d, J=3.0 Hz), 5.46 (2H, s), 4.04 (2H, s).

3-(1H-indol-6-yl)benzoic acid (I-12): Mass calculated for $C_{15}H_{11}NO_2$: 237; LCMS: 220.1 (M+H—H$_2$O)$^+$; $^1$H NMR (400 MHz, DMSO-d$_6$) δ ppm 8.21 (1H, s), 7.93 (1H, d, J=7.3 Hz), 7.89 (1H, d, J=7.3 Hz), 7.67 (1H, s), 7.64 (1H, d, J=7.3 Hz), 7.58 (1H, t, J=7.9 Hz), 7.41 (1H, br), 7.33 (1H, d, J=7.9 Hz), 6.47 (1H, s).

Synthesis of 3-((1-(3-methoxyphenyl)-1H-indol-6-yl)methyl)benzoic acid, compound (I-7): The acid, 3-((1H-indol-6-yl)methyl)benzoic acid, 20 mg, was dissolved in 4 ml DMSO, and 18 mg 3-iodoanisole, 12 mg potassium hydroxide and 5 mg Cu$_2$O catalyst were added. The mixture was protected by N$_2$ and stirred for 24 hours at 135° C. After cooling to room temperature, 1 ml 25% NaOH in H$_2$O was added, The mixture was stirred for 3 hours at room temperature, then adjusted to pH 3.0 using 2M HCl. The solution was extracted with CH$_2$Cl$_2$, 3×15 ml. The organic solvent was combined and dried with Na$_2$SO$_4$, then evaporated to dryness. The final product was purified by HPLC using acetonitrile/H$_2$O as eluent. The acetonitrile was removed from the eluent, the eluent frozen and lyophilized. After lyophilization, 5.0 mg of the target compound was obtained as a grey powder.

Analysis: Mass calculated for $C_{23}H_{19}NO_3$: 357; LCMS: 358.7 (M+H)$^+$; $^1$H NMR (400 MHz, DMSO-d$_6$) δ ppm 7.81 (1H, s), 7.74 (1H, d, J=6.8 Hz), 7.61 (1H, d, J=3.0 Hz), 7.58 (1H, d, J=7.8 Hz), 7.49 (3H, m), 7.39 (1H, t, J=6.8 Hz), 7.14 (1H, d, J=7.8 Hz), 7.08 (1H, s), 7.01 (1H, d, J=7.8 Hz), 6.96 (1H, d, J=7.8 Hz), 6.64 (1H, d, J=2.4 Hz), 4.12 (2H, s), 3.82 (3H, s).

Synthesis of 3-((6-(3-methoxyphenyl)-1H-indol-1-yl)methyl)benzoic acid, compound (I-11): Indole-6-boronic acid, 242 mg (1.5 mmol) and 3-iodoanisole, 351 mg (1.5 mmol) were added into a 50 ml round-bottomed flask containing 10 ml THF, 200 mg Pd(PPh$_3$)$_4$ was added, followed by 2 ml 2M K$_2$CO$_3$. The mixture was stirred and heated to 80° C. under N$_2$ protection for over 4 hours. After the reaction was completed as indicated by TLC, the mixture was cooled to room temperature, 10 ml H$_2$O was added and the product extracted with ethyl acetate (3×10 ml). The organic solvent was combined and dried with anhydrous Na$_2$SO$_4$, filtered and evaporated to dryness. The crude product was purified by chromatographic column using hexane:ethyl acetate (7:1) as eluent. The ester, 130 mg, was obtained as a pale yellow solid, yield 65%. The ester, 15 mg, was dissolved in 4 ml anhydrous DMF and 50 mg NaH was added. The mixture was stirred at room temperature for about 1 hour, then methyl-3-(bromomethyl)benzoate, 23 mg (0.1 mmol) was added, and the solution was stirred overnight. Then, 1 ml 25% NaOH in H$_2$O was added and the solution was stirred for 3 hours at room temperature, and the pH was adjusted to 3.0 using 2M HCl. The solution was extracted with CH$_2$Cl$_2$ (3×15 ml). The organic solvent was combined and dried with Na$_2$SO$_4$, then evaporated to dryness. The final product was purified by HPLC using acetonitrile/H$_2$O as eluent. The acetonitrile was removed from the eluent, the eluent frozen and lyophilized. After lyophilization, 5.0 mg target compound was obtained as a grey powder.

Analysis: 6-(3-methoxyphenyl)-1H-indole: Mass calculated for $C_{15}H_{13}N_0$: 223; LCMS: 224.6 (M+H)$^+$; $^1$H NMR (400 MHz, DMSO-d$_6$) δ ppm 7.63 (1H, s), 7.60 (1H, d, J=7.9 Hz), 7.37 (1H, t, J=3.0 Hz), 7.34 (1H, d, J=7.9 Hz), 7.30 (1H, dd, J=1.8 Hz, J=7.9 Hz), 7.23 (1H, d, J=7.9 Hz), 7.17 (1H, br), 6.89 (1H, dd, J=1.8 Hz, J=8.5 Hz), 6.44 (1H, s), 3.83 (3H, s).

3-((6-(3-methoxyphenyl)-1H-indol-1-yl)methyl)benzoic acid (I-11): Mass calculated for $C_{23}H_{19}NO_3$: 357; LCMS: 358.7 (M+H)$^+$; $^1$H NMR (400 MHz, DMSO-d$_6$) δ ppm 7.82 (1H, s), 7.81 (1H, s), 7.77 (1H, s), 7.62 (1H, d, J=8.5 Hz), 7.57 (1H, d, J=2.4 Hz), 7.46 (2H, m), 7.34 (2H, m), 7.23 (1H, d, J=7.3 Hz), 7.18 (1H, s), 6.88 (1H, d, J=7.9 Hz), 6.53 (1H, s), 5.60 (2H, s), 3.82 (3H, s).

Following the same or similar procedure the following compounds were made:

3-(6-(3-carboxybenzyl)-1H-indol-1-yl)benzoic acid (I-6): Mass calculated for $C_{23}H_{17}NO_4$, 371, LCMS: 372.6 (M+H)$^+$; $^1$HNMR (400 MHz, DMSO-d$_6$) δ ppm 8.02 (1H, s), 7.95 (2H, br), 7.86 (1H, d, J=8.8 Hz), 7.78 (1H, s), 7.67 (1H, s), 7.59 (1H, d, J=7.8 Hz), 7.49 (2H, br), 7.39 (1H, d, J=7.8 Hz), 6.68 (2H, br), 6.56 (1H, s), 4.11 (2H, s).

3-((6-(3-hydroxyphenyl)-1H-indol-1-yl)methyl)benzoic acid (I-14): Mass calculated for $C_{22}H_{17}NO_3$: 343; LCMS: 344.1 (M+H)$^+$; $^1$H NMR (400 MHz, DMSO-d$_6$) δ ppm 8.07 (1H, s), 7.91 (1H, d, J=7.8 Hz), 7.74 (1H, d, J=6.8 Hz), 7.63 (1H, s), 7.59 (1H, d, J=8.8 Hz), 7.54 (1H, t, J=7.8 Hz), 7.36 (2H, m), 7.29 (2H, br), 7.18 (1H, s), 6.98 (1H, d, J=7.8 Hz), 6.44 (1H, s), 5.28 (2H, s).

3-(3-(1-(3-carboxybenzyl)-1H-indol-6-yl)phenoxy)methyl)benzoic acid (I-21): Mass calculated for $C_{30}H_{23}NO_5$: 477; LCMS: 478.1 (M+H)$^+$ $^1$H NMR (400 MHz, DMSO-d$_6$) δ ppm 8.07 (1H, s), 7.91 (1H, d, J=7.8 Hz), 7.79 (3H, m), 7.73 (1H, d, J=7.8 Hz), 7.62 (1H, d, J=7.8 Hz), 7.56 (1H, d, J=3.9 Hz), 7.53 (1H, d, J=7.8 Hz), 7.44 (2H, m), 7.33 (2H, m), 7.30 (1H, d, J=1.9 Hz), 7.25 (1H, d, J=7.8 Hz), 6.97 (1H, dd, J=8.8 Hz, J=1.9 Hz), 6.53 (1H, d, J=2.9 Hz), 5.60 (2H, s), 5.26 (2H, s).

3-((3-((6-(3-(4-methoxybenzyloxy)phenyl)-1H-indol-1-yl)methyl)benzoyloxy)methyl)benzoic acid (I-22): Mass calculated for $C_{39}H_{31}NO_6$: 597; LCMS: 598.1 (M+1)$^+$ $^1$H NMR (400 MHz, DMSO-d$_6$) δ ppm 8.02 (1H, s), 7.89 (1H, d, J=7.8 Hz), 7.78 (1H, d, J=6.8 Hz), 7.75 (1H, s), 7.68 (1H, d, J=7.8 Hz), 7.57 (2H, br), 7.50 (1H, t, J=7.8 Hz), 7.37 (2H, m), 7.31 (1H, s), 7.07 (1H, d, J=8.8 Hz), 6.92 (2H, m), 6.84 (1H, d, J=2.9 Hz), 6.69 (5H, m), 6.54 (1H, d, J=2.9 Hz), 5.45 (2H, s), 5.17 (2H, s), 3.71 (2H, s), 3.66 (3H, s).

Synthesis of Compounds (II-1 and II-2):

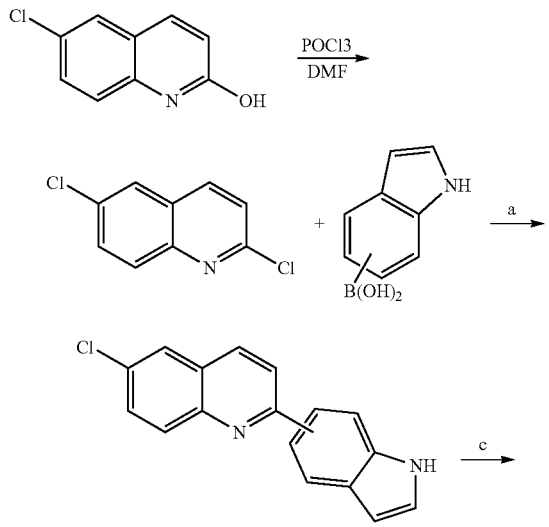

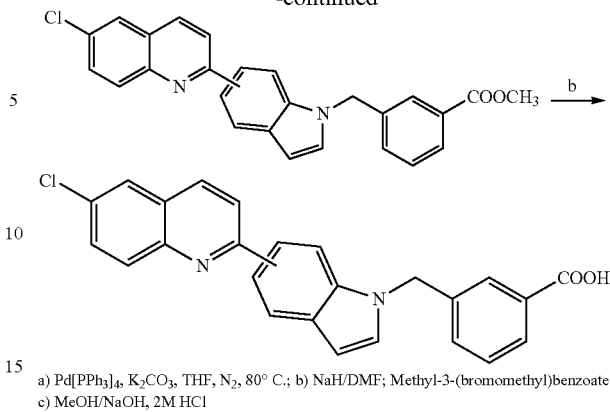

a) Pd[PPh$_3$]$_4$, K$_2$CO$_3$, THF, N$_2$, 80° C.; b) NaH/DMF; Methyl-3-(bromomethyl)benzoate c) MeOH/NaOH, 2M HCl Synthesis of 2,6-dichloro quinoline: 180 mg 6-chloro-2-hydroxy quinoline was treated by 3 ml POCl$_3$, the mixture was refluxed for 3 hours, the remaining POCl$_3$ was evaporated out. After cooling to room temperature, the residue was treated by cold water, the solid was filtered out and dried as green powder, yield: 90%. Following the general procedure in claim 5, the listed compounds were achieved. Mass calculated for $C_9H_5Cl_2N$: 198; LCMS: 200.1 (M+2)$^+$; $^1$HNMR (400 MHZ), DMSO-d$_6$) δ ppm 8.04 (1H, d, J=7.8 Hz), 7.97 (1H, d, J=8.8 Hz), 7.81 (1H, d, J=1.9 Hz), 7.68 (1H, dd, J=9.8 Hz, J=2.9 Hz), 7.42 (1H, d, J=8.8 Hz).

6-(6-chloro-2-quinolyl) indole: Mass calculated for $C_{11}H_{17}ClN_2$: 278; LCMS: 280.8 (M+2)$^+$; $^1$HNMR (400 MHz, DMSO-d$_6$) δ ppm 8.32 (1H, s), 8.11 (2H, t, J=8.8 Hz), 7.97 (1H, d, J=8.8 Hz), 7.88 (1H, dd, J=7.8 Hz, J=1.9 Hz), 7.80 (1H, d, J=1.9 Hz), 7.77 (1H, d, J=7.8 Hz), 7.64 (1H, dd, J=8.8 Hz, J=1.9 Hz), 7.32 (1H, t, J=2.9 Hz). 6.62 (1H, s).

5-(6-chloro-2-quinolyl) indole: Mass calculated for $C_{11}H_{17}ClN_2$: 278; LCMS: 279.1 (M+H)$^+$; $^1$HNMR (400 MHz, DMSO-d$_6$) δ ppm 8.44 (1H, s), 8.10 (3H, m), 7.99 (1H, d, J=8.8 Hz), 7.91 (1H, d, J=1.9 Hz), 7.64 (1H, dd, J=8.8 Hz, J=1.9 Hz), 7.53 (1H, d, J=8.8 Hz), 7.27 (1H, t, J=2.9 Hz), 6.68 (1H, s).

3-((6-(6-chloroquinolin-2-yl)-1H-indol-1-yl)methyl)benzoic acid (II-1): Mass calculated for $C_{25}H_{17}ClN_2O_2$: 412.8; LCMS: 413.3 (M+2)$^+$; $^1$H-NMR (400 MHZ), DMSO-d$_6$) δ ppm 8.53 (1H, s), 8.39 (1H, d, J=8.5 Hz), 8.24 (1H, d, J=8.5 Hz), 8.10 (2H, dd, J=8.5 Hz, J=1.8 Hz), 8.05 (1H, d, J=9.2 Hz), 7.83 (1H, dd, J=1.8 Hz, J=6.7 Hz), 7.79 (1H, s), 7.75 (1H, m), 7.62 (2H, m), 7.45 (2H, m), 6.68 (1H, d, J=3.0 Hz), 5.58 (2H, s).

3-((5-(6-chloroquinolin-2-yl)-1H-indol-1-yl)methyl)benzoic acid (II-2): Mass calculated for $C_{25}H_{17}ClN_2O_2$: 413; LCMS: 415.3 (M+2)$^+$; $^1$H-NMR (400 MHz, DMSO-d$_6$) δ ppm 8.41 (2H, m), 8.27 (1H, d, J=8.5 Hz), 8.10 (1H, d, J=2.4 Hz), 8.04 (2H, d, J=8.5 Hz), 7.81 (2H, br), 7.72 (2H, m), 7.67 (1H, d, J=3.0 Hz), 7.48 (2H, m), 6.59 (1H, d, J=2.4 Hz), 5.67 (2H, s).

Synthesis of Compound (II-3):

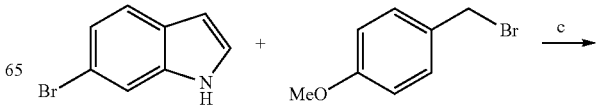

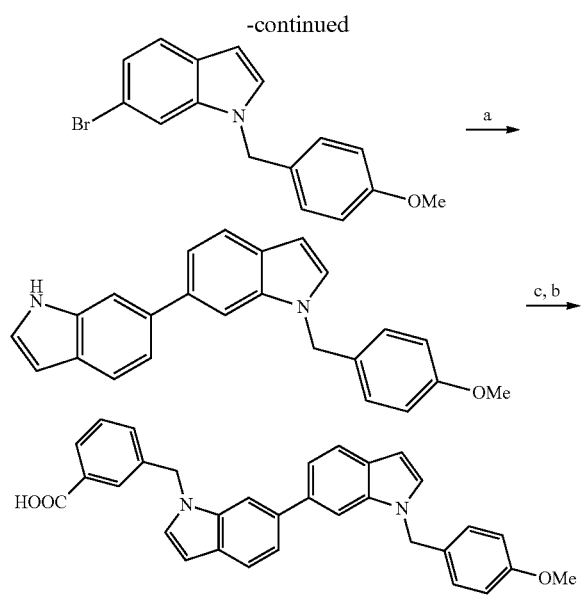

a) Pd[PPh₃]₄, K₂CO₃, THF, N₂, 80° C.; b) MeOH/NaOH, 2M HCl; c) NaH/DMF; Methyl-3-(bromomethyl)benzoate The 1-(4-methoxyphenyl)methyl-6-bromoindole was made using the aryl coupling protocols as described herein. The 1-(4-methoxyphenyl)methyl-6-bromoindole was then used in another aryl coupling reaction with 6-bromo-1H-indole to form the corresponding bis-indole intermediate, which was subjected to saponification to yield compound II-3 as depicted above.

1-(4-methoxyphenyl)methyl-6-bromoindole: $^1$H-NMR (400 MHZ), DMSO-d$_6$) δ ppm 7.73 (1H, s), 7.51 (2H, br), 7.17 (2H, d, J=8.5 Hz), 7.12 (1H, dd, J=1.2 Hz, J=8.5 Hz), 6.87 (2H, d, J=8.5 Hz), 6.49 (1H, d, J=3.0 Hz), 5.34 (2H, s), 3.70 (3H, s).

1-(4-methoxybenzyl)-1H,1'H-6,6'-biindole: Mass calculated for $C_{24}H_{20}N_2O$: 352; LCMS: 335.8 $(M+H-H_2O)^+$; $^1$HNMR (400 MHz, DMSO-d$_6$) δ ppm 7.72 (1H, s), 7.68 (1H, m), 7.62 (1H, s), 7.61 (1H, d, J=3.6 Hz), 7.59 (1H, d, J=4.3 Hz), 7.48 (1H, d, J=3.0 Hz), 7.34 (1H, s), 7.31 (1H, d, J=7.3), 7.21 (2H, d, J=8.5 Hz), 6.87 (2H, d, J=8.5 Hz), 6.47 (1H, d, J=3.0 Hz), 6.43 (1H, s), 5.42 (2H, s), 3.68 (3H, s).

3-((1'-(4-methoxybenzyl)-1H,1'H-6,6'-biindol-1-yl)methyl)benzoic acid (II-3): Mass calculated for $C_{32}H_{26}N_2O_3$: 486; LCMS: 487.8 $(M+H)^1$; $^1$H-NMR (400 MHz, DMSO-d$_6$) δ ppm 7.83 (2H, br), 7.69 (2H, d, J=8.5 Hz), 7.60 (2H, t, J=8.5 Hz), 7.55 (2H, t, J=3.0 Hz), 7.46 (2H, br), 7.35 (2H, m), 7.20 (2H, d, J=8.5 Hz), 6.84 (2H, d, J=8.5 Hz), 6.45 (1H, d, J=3.0 Hz), 6.51 (1H, d, J=3.0 Hz), 5.60 (2H, s), 5.39 (2H, s), 3.66 (3H, s).

Compound Analysis for gp41 Binding and Cell-Cell Fusion Inhibition:

Compounds were validated for binding activity with a biochemical assay, and for biological activity with a cell-cell fusion (CCF) assay.

The binding assay is a competitive inhibition fluorescence assay for the hydrophobic pocket utilizing a receptor Fe(env2.0)$_3$ selective for the hydrophobic pocket and a fluorescently labeled probe peptide derived from the C-peptide sequence that binds in the pocket (see Cai, L.; Gochin, M. A Novel Fluorescence Intensity Screening Assay Identifies New Low Molecular Weight Inhibitors of the gp41 Coiled Coil Domain of HIV-1. *Antimicrob Agents Chemother* 2007, 51, 2388-95). Association between the C-peptide and receptor leads to fluorescence quenching, which is reversed in the presence of an inhibitor. Compounds are typically measured in eleven serial dilutions. The assay is quantitative and provides the binding constant ($K_I$) of the inhibitor.

For the CCF assay, TZM-bl target cells containing a luciferase gene governed by an LTR promoter were used, and HL2-3 effector cells expressing HIV-1 env and Tat. These cells were obtained from the NIH Research and Reference Reagents Program (see Derdeyn, C. A.; Decker, J. M.; Sfakianos, J. N.; Wu, X.; O'Brien, W. A.; Ratner, L.; Kappes, J. C.; Shaw, G. M.; Hunter, E. Sensitivity of human immunodeficiency virus type 1 to the fusion inhibitor T-20 is modulated by coreceptor specificity defined by the V3 loop of gp120. *J Virol* 2000, 74, 8358-67; Platt, E. J.; Durnin, J. P.; Kabat, D. Kinetic factors control efficiencies of cell entry, efficacies of entry inhibitors, and mechanisms of adaptation of human immunodeficiency virus. *J Virol* 2005, 79, 4347-56; Wei, X.; Decker, J. M.; Liu, H.; Zhang, Z.; Arani, R. B.; Kilby, J. M.; Saag, M. S.; Wu, X.; Shaw, G. M.; Kappes, J. C. Emergence of resistant human immunodeficiency virus type 1 in patients receiving fusion inhibitor (T-20) monotherapy. *Antimicrob Agents Chemother* 2002, 46, 1896-905). TZM-bl cells, 25,000 in 50 μl of culture medium, are plated in 96-well plates and grown in a CO$_2$ incubator for 18 hours. The medium is then exchanged for 49 μl reduced serum medium, and 1 μl DMSO, or 1 μl compound in DMSO, is added, followed by 50 μl of HL2-3 cells (50,000 cells) in reduced serum medium. Compounds are typically measured in ten serial dilutions. The cell mixture is incubated for 6-8 hours, and cell-cell fusion quantitated using Luciferase Assay Reagent (Promega). Compounds were also examined for cytotoxicity using a commercial luciferase expression-based test on TZM-bl cells (Promega), after 24 hour exposure of cells to compound.

While not wishing to be bound by theory, experimental data on binding and fusion inhibition suggest an excellent correlation between binding affinity ($K_I$) and IC$_{50}$ for cell fusion. This confirms the mechanism of inhibition as binding in the hydrophobic pocket. Binding was measured as an increase in fractional fluorescence; Fusion inhibition was measured as a decrease in luminescence of the mixture of TZM-bl cells and HL-2/3 cells after incubation with test compound. Toxicity of the compounds to TZM-bl cells was also tested to ensure that the luminescence decrease was not simply due to cell death (CC$_{50}$, toxicity).

Table 2 shows the KI, IC$_{50}$, and CC$_{50}$ data as determined by the tests described above. The compound designations in Table 3 are consistent with those of Tables 1 and 2 above. Compounds described herein have an IC$_{50}$ as against HIV-1 cell fusion of less than about 650 μM, or less than about 300 μM, or less than about 200 μM, or less than about 100 μM, or less than about 50 μM, or less than about 25 μM, or less than about 10 μM, or less than about 5 μM, or less than about 1 μM.

TABLE 3

| Compound | MW | KI (μM) | IC$_{50}$ (μM) | CC$_{50}$ (μM) |
|---|---|---|---|---|
| I-1 | 251.09 | 2.5 ± 0.5 | 3.2 ± 0.5 | >500 |
| I-2 | 371.40 | 3.4 ± 0.5 | 3.7 ± 0.5 | 100 |
| I-3 | 323.30 | 393 ± 31 | >100 | >100 |
| I-4 | 385.41 | 21.7 ± 1.6 | 130 ± 5 | >200 |
| I-5 | 514.57 | 1.4 ± 0.4 | 2.9 ± 0.2 | >100 |
| I-6 | 323.30 | 45 ± 5 | 186 ± 16 | >400 |
| I-7 | 357.40 | 2.1 ± 0.25 | 1.8 ± 0.4 | >100 |
| I-8 | 279.29 | 44.1 ± 1.8 | 141 ± 59 | >100 |
| I-9 | 251.09 | 18 ± 5 | 48 ± 4 | >400 |
| I-10 | 371.40 | 34.5 ± 3.7 | >400 | >400 |

TABLE 3-continued

| Compound | MW | KI (µM) | IC$_{50}$ (µM) | CC$_{50}$ (µM) |
|---|---|---|---|---|
| I-11 | 357.40 | 2.6 ± 0.3 | 8.1 ± 1.8 | >100 |
| I-12 | 237.25 | 13.9 ± 0.9 | 79 ± 15 | >100 |
| I-13 | 385.41 | 8.9 ± 3.1 | 23 ± 4 | >400 |
| I-14 | 343.12 | 3.3 ± 0.4 | 14 ± 2.3 | >100 |
| II-1 | 412.9 | 5.8 ± 0.6 | 13 ± 3.4 | 93 |
| II-2 | 412.9 | 1.7 ± 0.2 | 8.3 ± 2.7 | 156 |
| I-15 | 252.3 | >100 | 24 ± 11 | ~63 |
| I-16 | 296.3 | 15.3 ± 2.2 | 37.2 ± 2.7 | >100 |
| I-17 | 280.3 | 13.2 ± 1.1 | >100 | >100 |
| I-18 | 267.3 | 33.9 ± 4.0 | >100 | >100 |
| I-19 | 267.3 | 4.4 ± 0.5 | 19 ± 2 | >100 |
| I-20 | 280.3 | 6.7 ± 1.1 | 18 ± 2 | >100 |
| I-21 | 477.5 | 1.14 ± 0.18 | 9.1 ± 0.46 | >100 |
| I-22 | 597.7 | 1.22 ± 0.25 | 1.5 ± 0.17 | >100 |
| II-3 | 486.6 | 0.43 ± 0.03 | 0.8 ± 0.2 | 18.9 ± 2.9 |

The ability of the compounds to inhibit HIV-1 infectivity was assessed using standard assays as reported in the literature. See: 1) Desmezieres, E.; Gupta, N.; Vassell, R.; He, Y.; Peden, K.; Sirota, L.; Yang, Z.; Wingfield, P.; Weiss, C. D. *J Virol* 2005, 79, 4774, and 2) Lackman-Smith, C.; Osterling, C.; Luckenbaugh, K.; Mankowski, M.; Snyder, B.; Lewis, G.; Paull, J.; Profy, A.; Ptak, R. G.; Buckheit, R. W., Jr.; Watson, K. M.; Cummins, J. E.; Sanders-Beer, B. E. *Antimicrob Agents Chemother* 2008. Table 4 shows the viral infectivity data, reported in µM concentration as IC$_{50}$'s.

TABLE 4

| Cpd | IC$_{50}$ (viral infectivity inhibition, HXB2[1]) | IC$_{50}$ (viral infectivity inhibition, IIIB[2]) | IC$_{50}$ (viral infectivity inhibition, Ba-L[3]) |
|---|---|---|---|
| I-1 | | 99.9 | 44.7 |
| I-5 | 17 | ≧100 | 92.1 |
| I-7 | | 61.5 | 67.7 |
| I-11 | | 57.4 | 47.4 |

As well, the compounds were evaluated in an HIV-1 Ba-L virus neutralization assay in MAGI cells. Details of the HIV-1 virus neutralization assay, using Pseudovirus HIV-1 BAL (CCR5-tropic strain)+HeLa-R5-16 target cells are provided below:

1. Plate target cells: split U87-CD4-X4 1:3 from 90% to 96 well plate
2. Incubate at 37° C. for 24 hr
3. Prepare 2× virion/polybrene
4. Prepare 2× inhibitor dilutions: (begin all at 200 µM, made by diluting DMSO stock in medium and prepare serial 1:3 dilutions.
5. Prepare virus/inhibitor dilutions by adding 100 µl virus to 100 µl 2× inhibitors.
6. Incubate at 37° C. for 1 hr
7. Aspirate media and apply 50 µl of virus/inhibitor dilutions
8. Incubate overnight at 37° C.
9. Aspirate virus and replace with 100 µl media.
10. Incubate additional 24 hr at 37° C.
11. Aspirate media.
12. Add 50 µl CCLR lysis buffer to all wells. Rock at RT for 30 min.
13. Transfer 20 µl lysate to 96 well white plate with same plate plan as infection.
14. Read on luminometer with 50 µl substrate (Luciferase substrate: Promega #E151A)

Table 5 shows the results, where IC$_{50}$, IC$_{90}$, TC$^{50}$ are all reported in µM units.

TABLE 5

| Compound | % Serum | IC$_{50}$ | IC$_{90}$ | TC$_{50}$ | TI (TC$_{50}$/IC$_{50}$) |
|---|---|---|---|---|---|
| I-1 | 2% | 15.5 | 58 | >100 | >6.45 |
| | 5% | 34.8 | 89.4 | >100 | >2.87 |
| | 10% | 44.7 | >100 | >100 | >2.24 |
| I-7 | 2% | 15.8 | >100 | >100 | >6.33 |
| | 5% | 34 | >100 | >100 | >2.94 |
| | 10% | 67.7 | >100 | >100 | >1.48 |
| I-11 | 2% | 18 | >100 | 67.5 | 3.75 |
| | 5% | 36.6 | >100 | >100 | >2.73 |
| | 10% | 47.4 | >100 | >100 | >2.11 |
| I-5 | 2% | 14.6 | 71.2 | >100 | >6.85 |
| | 5% | 49.6 | 93.6 | >100 | >2.02 |
| | 10% | 92.1 | >100 | >100 | >1.09 |
| I-22 | 2% | 13.8 | 31.1 | 58.9 | 4.27 |
| | 5% | 18.7 | 76.4 | >100 | >5.35 |
| | 10% | 22.6 | 91.7 | >100 | >4.42 |

While this invention has been described in terms of a few preferred embodiments, it is not limited to the specifics presented above. Many variations on the above-described preferred embodiments, may be employed. Therefore, the invention should be interpreted with reference to the following claims.

What is claimed is:

1. A compound, according to formula Va:

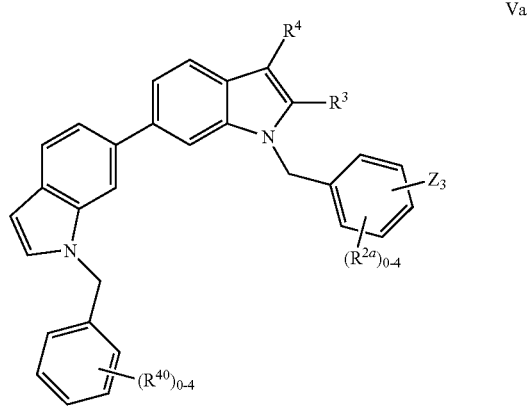

wherein:

$Z_3$ is —(CH$_2$)$_{0-3}$CO$_2$R$^a$ or H;

each R$^a$ is independently H, C$_{1-6}$alkyl, C$_{3-8}$cycloalkyl, C$_{4-11}$cycloalkylalkyl, C$_{6-10}$aryl, C$_{7-16}$arylalkyl, 3-10 membered heteroalicyclyl, 4-11 membered heteroalicyclylalkyl, 5-15 membered heteroaryl or 6-16 membered heteroarylalkyl;

each R$^{2a}$ is independently optionally substituted C$_{1-6}$alkyl, halo, —OC$_{1-6}$alkyl, —OH —N(C$_{1-6}$alkyl)$_2$, —N(H)C$_{1-6}$ alkyl, —CN, —NO$_2$, —C(O)C$_{1-6}$alkyl, —CO$_2$H, —CO$_2$C$_{1-6}$alkyl, —C(O)N(H)C$_{1-6}$alkyl or —C(O)N(C$_{1-6}$alkyl)$_2$;

each of R$^3$ and R$^4$ are, independently, —H, halo, optionally substituted C$_{1-6}$alkyl, optionally substituted C$_{3-8}$cycloalkyl, optionally substituted C$_{4-11}$cycloalkylalkyl, optionally substituted C$_{6-10}$aryl, optionally substituted C$_{7-16}$arylalkyl, optionally substituted 3-10 membered heteroalicyclyl, optionally substituted 4-11 membered heteroalicyclylalkyl, optionally substituted 5-15 membered heteroaryl or 6-16 membered heteroarylalkyl; and where each R$^{40}$ is independently C$_{1-6}$alkyl, halo, —OC$_{1-6}$ alkyl, —OH, —N(R$^{80a}$)$_2$, perhaloalkyl, —CN, —NO$_2$, —CO₂C$_{1-6}$alkyl or —C(O)NR$^{80a}$R$^{80a}$, where each R$^{80a}$ is independently H or C$_{1-6}$alkyl; and at least one of R$^{40}$ is —OC$_{1-6}$alkyl.

2. A compound, or pharmaceutically acceptable salt thereof, which is
- 3-((1H-indol-6-yl)methyl)benzoic acid (I-1);
- 3-((1-(4-methoxybenzyl)-1H-indol-6-yl)methyl)benzoic acid (I-2);
- 3-((3-(carboxycarbonyl)-1H-indol-6-yl)methyl)benzoic acid (I-3);
- 3-((1-(3-(carboxy)benzyl)-1H-indol-6-yl)methyl)benzoic acid (I-4);
- 3,3'-(1,1'-methylenebis(1H-indole-6,1-diyl))bis(methylene)dibenzoic acid (I-5);
- 3-(6-(3-carboxybenzyl)-1H-indol-1-yl)benzoic acid (I-6);
- 3-((1-(3-methoxyphenyl)-1H-indol-6-yl)methyl)benzoic acid (I-7);
- 3-((3-formyl-1H-indol-6-yl)methyl)benzoic acid (I-8);
- 3-((1H-indol-5-yl)methyl)benzoic acid (I-9);
- 3-((1-(3-carboxybenzyl)-1H-indol-5-yl)methyl)benzoic acid (I-10);
- 3-((6-(3-methoxyphenyl)-1H-indol-1-yl)methyl)benzoic acid (I-11);
- 3-(1H-indol-6-yl)benzoic acid (I-12);
- 3-(1-(3-carboxybenzyl)-1H-indol-5-yl)benzoic acid (I-13);
- 3-((6-(3-hydroxyphenyl)-1H-indol-1-yl)methyl)benzoic acid (I-14);
- 6-(3-nitrobenzyl)-1H-indole (I-15);
- 3-((1H-indol-6-yl)methyl)-4-nitrobenzoic acid (I-16);
- 3-((1H-indol-6-yl)methyl)-4-methoxybenzoic acid (I-17);
- 3-((1H-indol-6-yl)methyl)-5-hydroxybenzoic acid (I-18);
- 3-((1H-indol-6-yl)methyl)-4-hydroxybenzoic acid (I-19);
- 3-((1H-indol-6-yl)methyl)-5-methoxybenzoic acid (I-20);
- 3-((3-(1-(3-carboxybenzyl)-1H-indol-6-yl)phenoxy)methyl)benzoic acid (I-21);
- 3-((3-((6-(3-(4-methoxybenzyloxy)phenyl)-1H-indol-1-yl)methyl)benzoyloxy)methyl)benzoic acid (I-22);
- 3-((6-(6-chloroquinolin-2-yl)-1H-indol-1-yl)methyl)benzoic acid (II-1);
- 3-((5-(6-chloroquinolin-2-yl)-1H-indol-1-yl)methyl)benzoic acid (II-2) or
- 3-((1'-(4-methoxybenzyl)-1H,1'H-6,6'-biindol-1-yl)methyl)benzoic acid (II-3).

3. A pharmaceutical composition comprising the compound according to claim 2 and a pharmaceutically acceptable carrier.

4. A unit dosage formulation comprising the pharmaceutical composition of claim 3.

5. A pharmaceutical composition comprising the compound according to claim 1 and a pharmaceutically acceptable carrier.

6. A unit dosage formulation comprising the pharmaceutical composition of claim 5.

* * * * *